(12) United States Patent
Yamasaki

(10) Patent No.: US 8,778,266 B2
(45) Date of Patent: Jul. 15, 2014

(54) SLIDE PROCESSING APPARATUS

(75) Inventor: Mitsuo Yamasaki, Kobe (JP)

(73) Assignee: Sysmex Corporation, Kobe (JP)

( * ) Notice: Subject to any disclaimer, the term of this patent is extended or adjusted under 35 U.S.C. 154(b) by 106 days.

(21) Appl. No.: 13/362,514

(22) Filed: Jan. 31, 2012

(65) Prior Publication Data

US 2012/0201721 A1 Aug. 9, 2012

(30) Foreign Application Priority Data

Feb. 3, 2011 (JP) ................................ 2011-021278

(51) Int. Cl.
*G01N 21/00* (2006.01)
(52) U.S. Cl.
USPC .................. 422/65; 422/63; 422/64; 422/66; 422/67; 436/180; 700/245
(58) Field of Classification Search
USPC ................ 422/536, 63–67; 436/180; 700/245
See application file for complete search history.

(56) References Cited

U.S. PATENT DOCUMENTS 7,790,107 B2 * 9/2010 Nakaya ........................... 422/65

FOREIGN PATENT DOCUMENTS

JP 2006-38781 A 2/2006

* cited by examiner

*Primary Examiner* — Jyoti Nagpaul
(74) *Attorney, Agent, or Firm* — Brinks Gilson & Lione

(57) ABSTRACT

A slide processing apparatus is disclosed. The apparatus comprise a liquid transporter for transporting a staining liquid reserved in a first liquid container and a washing liquid reserved in a second liquid container; a first instruction receiver for receiving a first instruction that instructs to initiate preparation of a slide stained with the staining liquid; a second instruction receiver for receiving a second instruction that instructs to initiate washing of a housing element which accommodates therein a slide to be stained; and a controller. When receiving the first instruction, the controller performs staining of the slide accommodated in the housing element by causing the liquid transporter to transport the staining liquid into the housing element. When receiving the second instruction, the controller performs washing of the housing element by causing the liquid transport to transport the washing liquid into the housing element.

19 Claims, 20 Drawing Sheets

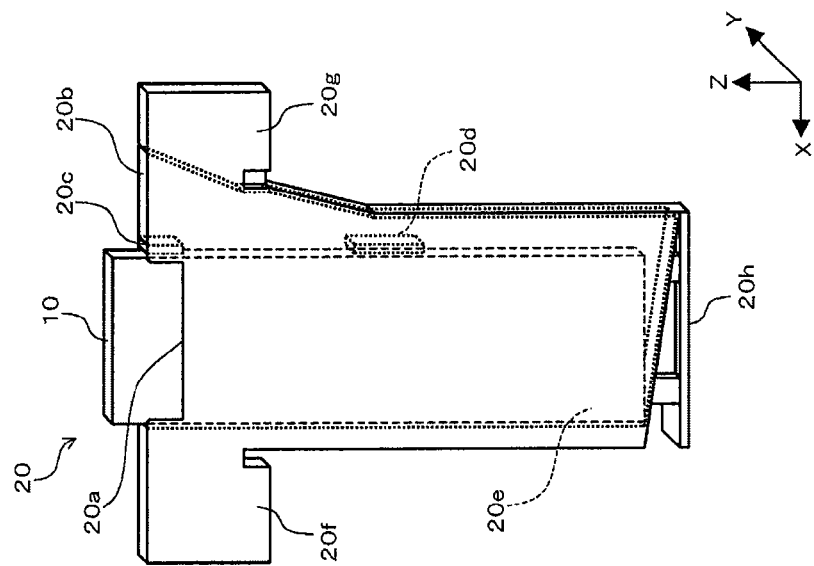
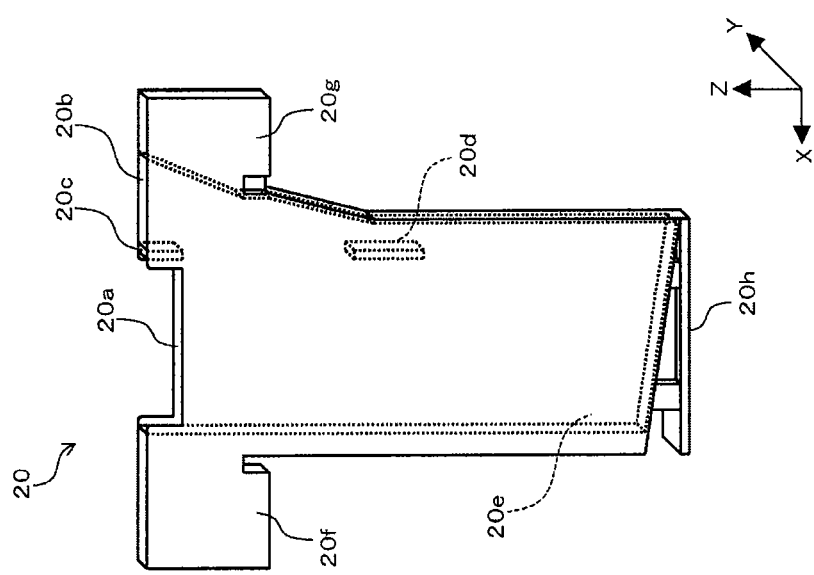

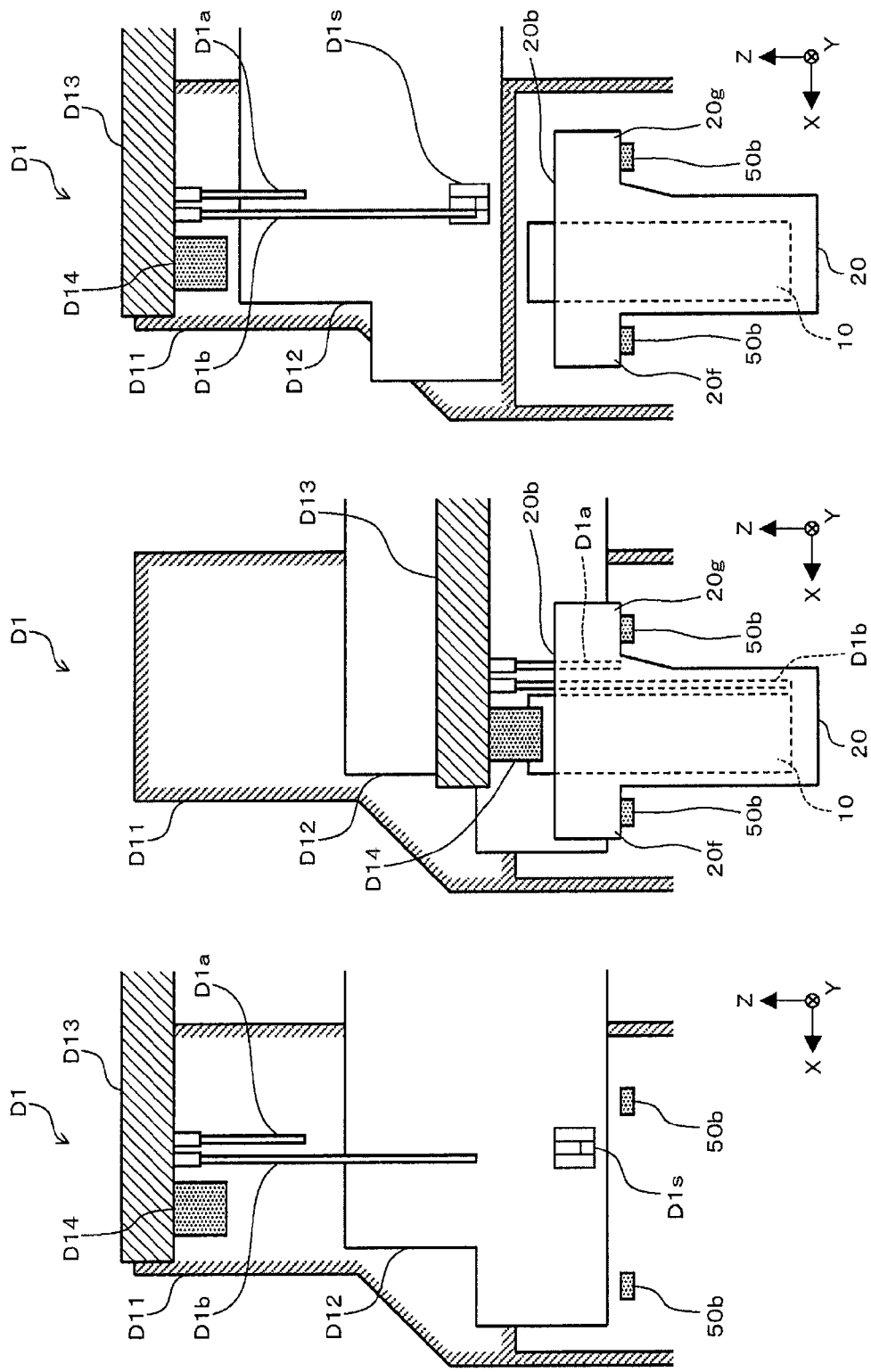

SLIDE PROCESSING APPARATUS

RELATED APPLICATIONS

This application claims priority under 35 U.S.C. §119 to Japanese Patent Application No. 2011-021278 filed on Feb. 3, 2011, the entire content of which is hereby incorporated by reference.

BACKGROUND OF THE INVENTION

1. Field of the Invention

The present invention relates to a slide processing apparatus for processing a slide within a cassette.

2. Description of the Related Art

There are known conventional specimen staining apparatuses for holding a smeared specimen on a slide enclosed in a specimen cassette and automatically performing a staining process on the held specimen (for example, Japanese Laid-Open Patent Publication No. 2006-38781). The specimen staining apparatus disclosed in Japanese Laid-Open Patent Publication No. 2006-38781 stains a specimen by injecting a staining liquid into a specimen cassette which holds the specimen, and after the staining process washes the specimen by injecting water into the specimen cassette.

In the specimen staining apparatus disclosed in Japanese Laid-Open Patent Publication No. 2006-38781, staining liquid may adhere inside the specimen cassette following repeated use of the specimen cassette. Therefore, in order to repeatedly use the specimen cassette, the user must manually wash the specimen cassette to remove the staining liquid adhered inside the specimen cassette.

SUMMARY OF THE INVENTION

A first aspect of the present invention is a slide processing apparatus comprising: a liquid transporter for transporting a staining liquid reserved in a first liquid container and a washing liquid reserved in a second liquid container; a first instruction receiver for receiving a first instruction that instructs to initiate preparation of a slide stained with the staining liquid; a second instruction receiver for receiving a second instruction that instructs to initiate washing of a housing element which accommodates therein a slide to be stained; and a controller, wherein, when receiving the first instruction, the controller performs staining of the slide accommodated in the housing element by causing the liquid transporter to transport the staining liquid into the housing element; and, when receiving the second instruction, the controller performs washing of the housing element by causing the liquid transport to transport the washing liquid into the housing element.

BRIEF DESCRIPTION OF THE DRAWINGS

FIGS. 3(a) and 3(b) are perspective views showing the structure of an embodiment of a cassette;

FIGS. 4(a)-4(c) show the operation of the staining unit of the embodiment;

DETAILED DESCRIPTION OF THE PREFERRED EMBODIMENTS

The present embodiment is an application of the invention in a clinical sample processing apparatus for preparing a smear sample from a blood sample. The clinical sample processing apparatus of the present embodiment is provided with a smear preparation apparatus and a transport device. Note that the necessity of preparing a smear sample is usually determined based on blood sample analysis results of a blood analyzer or the like at a previous stage. When preparing a smear sample, a sample rack holding a sample container which contains a sample is placed in the transport device. Subsequently, the sample rack is moved by the transport device and a smear sample is prepared by the smear preparation apparatus.

The embodiment of the clinical sample processing apparatus is described below with reference to the drawings.

Figure 1:
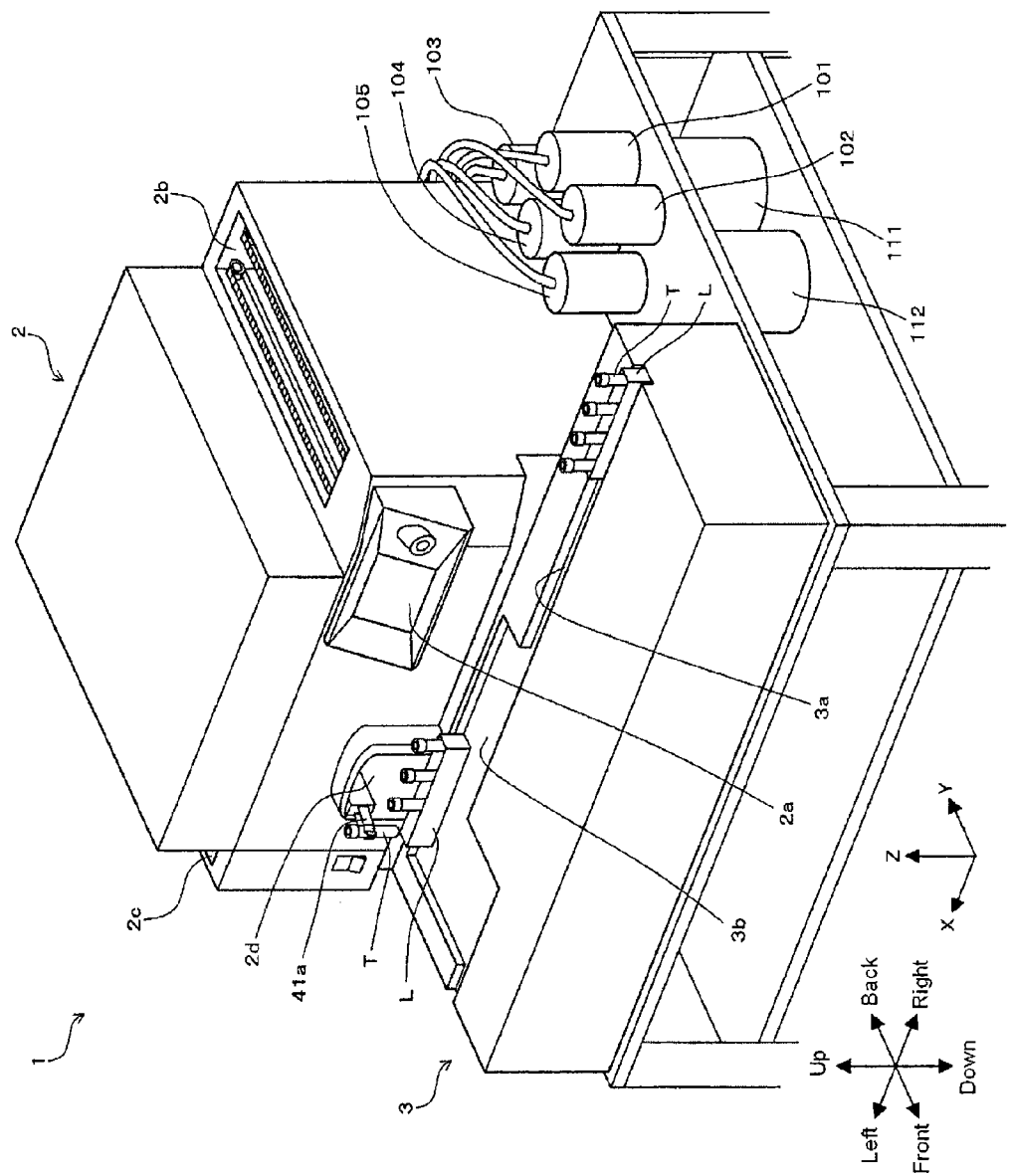
FIG. 1 is a perspective view showing the structure of an embodiment of a clinical sample processing apparatus.

FIG. 1 is a perspective view showing the structure of a clinical sample processing apparatus 1. The clinical sample processing apparatus 1 is provided with a smear sample preparation device 2 and a transport device 3. Note that below the X-axis positive direction is referred to as the left direction, the X-axis negative direction is the right direction, the Y-axis positive direction is the backward direction, the Y-axis negative direction is the forward direction, the Z-axis positive direction is the upward direction, and the Z-axis negative direction is the downward direction.

The smear sample preparation device 2 is provided with an operation display unit 2a configured by a touch panel disposed on the front surface of a cover. openings 2b and 2c are respectively formed at the top right and top left of the front surface of the cover of the smear sample preparation device 2. The smear sample preparation device 2 also has a hand unit 41a for holding a sample container T through an opening 2d. The user controls the smear sample preparation device 2 by operating the operation display unit 2a, sets a cassette 20 in a cassette receiver 47 (refer to FIG. 2; described later) through the opening 2c, and removes the cassette 20 deposited in the cassette storage unit 51 (refer to FIG. 2; described later) through the opening 2c.

Bottle 101 through 105 for containing staining liquid and the like to be used by a staining unit 50 (described later) are connected to the smear sample preparation device 2. In the present embodiment, the bottles 101 through 105 respectively contain methanol, May-Grünwald solution (staining liquid), Giemsa solution (staining liquid), phosphate buffer solution (diluting liquid), and water for washing samples. Two chambers (a first methanol chamber 111 and a second methanol chamber 112) containing methanol are also connected to the smear sample preparation device 2.

Figure 5:
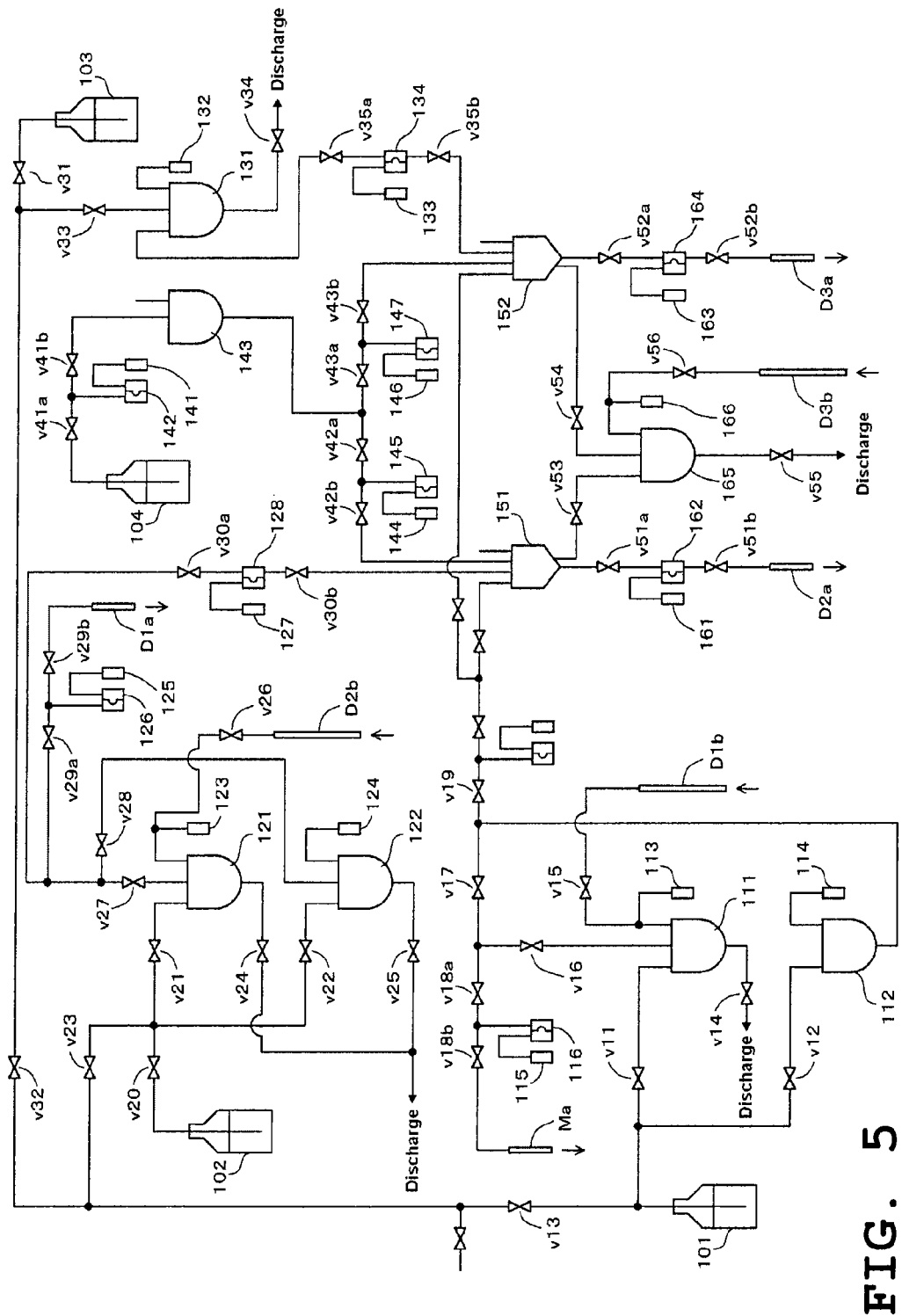
FIG. 5 briefly shows a fluid circuit diagram of the smear preparation apparatus of the embodiment.

Note that, in addition to the first methanol chamber 111 and second methanol chamber 112, the smear sample preparation device 2 is also connected to a first staining liquid chamber 121, second staining liquid chamber 122, staining liquid chamber 131, diluting liquid chamber 143, first mixing chamber 151, second mixing chamber 152, and discard chamber 165, as shown in FIG. 5.

The transport device 3 is arranged at the front side of the smear sample preparation device 2, and has a loader 3a and an ejector 3b. The transport device 3 transports a sample rack L that is positioned on the loader 3a to the ejector 3b. When the sample rack L is positioned in front of the hand unit 41a, the sample rack L is removed therefrom by the hand unit 41a and placed within the smear sample preparation device 2.

Figure 2:
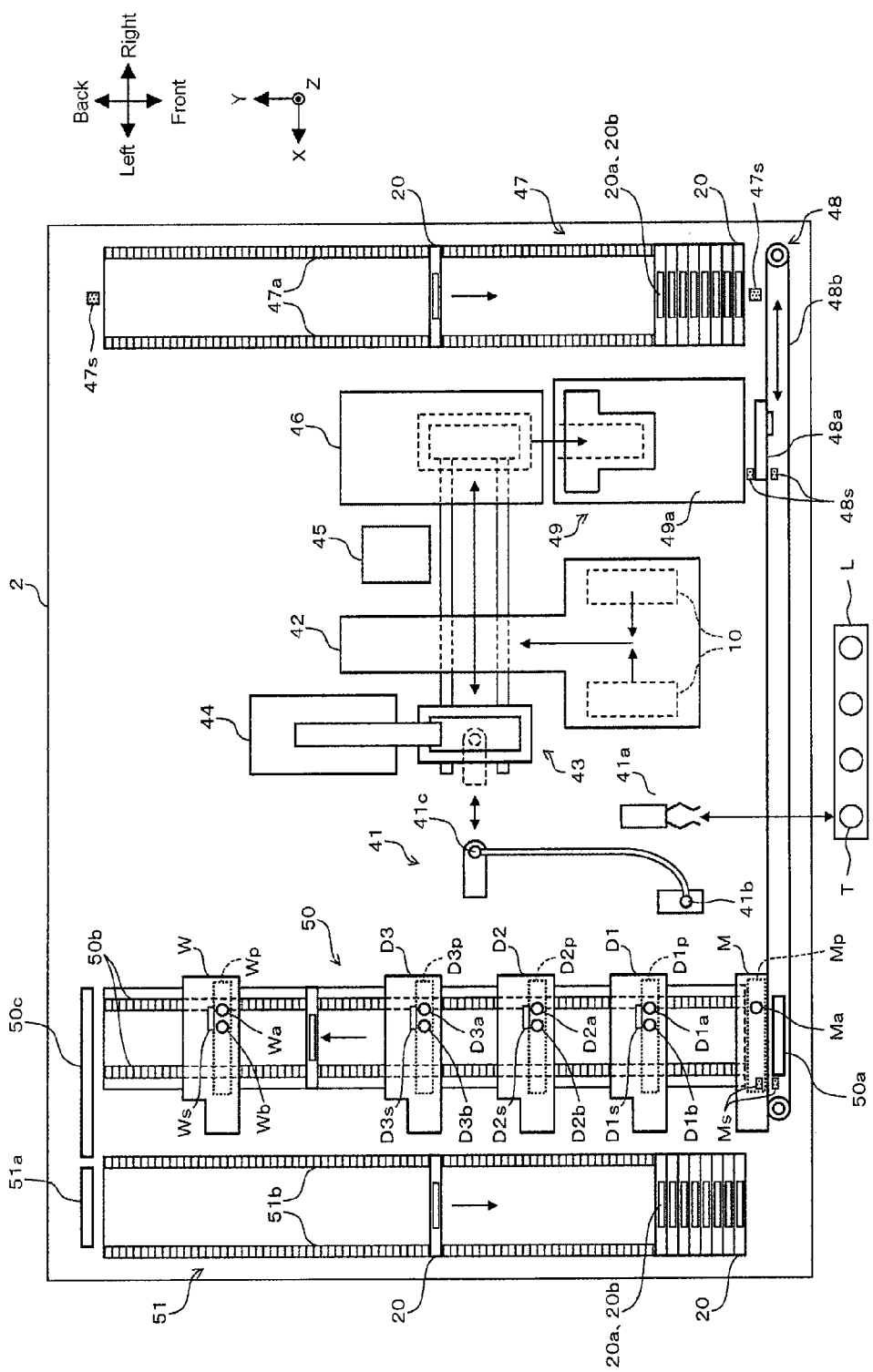
FIG. 2 is a plan view showing the structure of an embodiment of a smear preparation apparatus viewed from above.

FIG. 2 is a plan view showing the structure of the smear sample preparation device 2 viewed from above.

The smear sample preparation device 2 is provided with an aspirating/dispensing mechanism 41, slide glass supplier 42, slide glass cross-feeder 43, smearing mechanism 44, smear drier 45, printer 46, cassette receiver 47, cassette cross-feeder 48, cassette rotator 49, staining unit 50, and cassette storage unit 51.

The aspirating/dispensing mechanism 41 has a hand unit 41a, piercer (aspirating needle) 41b, and dispensing pipette 41c. A sample container T that is positioned in front of the hand unit 41a is removed from the sample rack L that is gripped by the hand unit 41a. Then, the blood sample accommodated in the sample container T is aspirated by the piercer 41b, and dripped by the laterally movable dispensing pipette 41c onto a slide glass 10 that is position in front of the smearing mechanism 44.

The slide glass supplier 42 holds a plurality of new slide glasses 10, and sequentially moves new slide glasses 10 up to the slide glass cross-feeder 43. The slide glass cross-feeder 43 moves the new slide glass 10 supplied from the slide glass supplier 42 in a leftward direction to position the slide glass 10 in front of the smearing mechanism 44.

The smearing mechanism 44 smears the blood sample when the blood sample is dripped onto the slide glass 10 positioned in front of the smearing mechanism 44. The slide glasses 10 bearing the smeared blood samples are moved in the rightward direction by the slide glass cross-feeder 43 and positioned directly below the printer 46 and in front of the smear drier 45. The smear drier 45 dries the blood sample smeared on the slide glass 10 positioned in front of the smear drier 45 via a fan (not shown in the drawing). The printer 46 is a printer (not shown in the drawing) that prints the sample number, day, receipt number, name and the like on the end of the slide glass 10.

The cassette receiver 47 has a belt 47a that is movable in a forward direction, and transmission type sensors 47s configured by a light emitter and a light receiver disposed near the front end and the back end of the belt 47a. The user can place an empty cassette 20 on the belt 47a through the opening 2b (refer to FIG. 1). The empty cassette 20 placed on the belt 47a is transported by the moving belt 47a in a forward direction. The sensors 47s detect whether a cassette 20 is placed on the belt 47a.

FIGS. 3(a) and (b) are perspective views showing the structure of the cassette 20. Note that FIGS. 3(a) and (b) show the coordinate axes of FIG. 2 when the cassette 20 is placed on the belt 47a.

Referring to FIG. 3(a), the cassette 20 is formed of resin, and has a thickness in the Y-axis direction so as to accommodate a slide glass 10 in a receiver 20e. Receiving holes 20a and 20b, which are laterally partitioned by a partition 20c, are formed on the top part of the cassette 20. The receiver 20e is formed within the cassette 20 with a partition 20d arranged in the downward direction of the partition 20c. Flanges 20f and 20g are formed on the lateral sides of the cassette 20, and the bottom surface of the flanges 20f and 20g are disposed on the belt 47a of FIG. 2 and maintained thus by the bottom surface of the flanges 20f and 20g. A bottom part 20h is formed below the cassette 20. The slide glass 20 can be inserted from the top side through the receiving hole 20a.

FIG. 3(b) is a perspective view showing the slide glass 10 accommodated in the cassette 20, as shown in FIG. 3(b), when the slide glass 10 is accommodated, there is a gap in the region on the right side of the partitions 20c and 20d in the receiver 20e. This gap allows the insertion of a pipette through the receiving hole 20b even when a slide glass 10 is accommodated in the cassette 20.

Returning to FIG. 2, the cassette cross-feeder 48 has a cassette support 48a, a laterally movable belt 48b, and transmission type sensors 48s configured by a light emitter and a light receiver. The cassette support 48a is attached to the belt 48b so as to support the bottom part 20h of the cassette 20 in an upward direction. An empty cassette 20 which is positioned in front of the cassette receiver 47 is supported by the cassette support 48a and transported leftward to in front of the cassette rotator 49. The sensors 48s are positioned in front of the cassette rotator 49 to detect whether a slide glass 10 is accommodated in the cassette 20 that is positioned in front of the cassette rotator 49 supported on the cassette support 48a.

The cassette rotator 49 has a flat surface 49a. The flat surface 49a is configured so as to rotate while maintaining parallel to the X-Y plane and parallel to the X-Z plane. The cassette rotator 49 receives the empty cassette 20 positioned in front of the cassette rotator 49, and the slide glass 10 is pushed from the printer 46 into the cassette 20. Then, the cassette 20, which contains the slide glass 10 on the flat surface 49a, is moved to the cassette support 48a of the cassette cross-feeder 48. Subsequently, the cassette 20 is transported leftward by the cassette cross-feeder 48 and positioned in front of the staining unit 50.

The staining unit 50 has a feed unit 50a, belt 50b that is movable in a backward direction, methanol processing unit M, stain processing units D1 through D3, wash processing unit W, and feed unit 50c. Each processing unit includes dispensing pipettes Ma, D1a, D2a, D3a, and Wa, collecting pipettes D1b, D2b<D3b, and Wb, and sensors Ms, D1s, D2s, D3s, and Ws.

The sensor Ms is a transmission type sensor configured by a light emitter and light receiver to detect when a cassette 20 is positioned at a position Mp (left end position of the cassette cross-feeder 48) for processing by the methanol processing unit M. The sensors D1s, D2s, D3s, and Ws are contact type sensors for detecting a cassette 20 respectively positioned at the stain processing units D1, D2, D3, and positions D1p, D2p, D3p, and Wp for processing by the wash processing unit W.

When the cassette 20 is detected by the sensor Ms, methanol is dispensed from the receiving hole 20b of the cassette 20 into the receiver 20e via the dispensing pipette Ma of the methanol processing unit M. At this time, the cassette 20 is supported by the cassette support 48a of the cassette crossfeeder 48. Thereafter, the cassette 20 is fed onto the belt 50b by the feeding unit 50a.

The cassette 20 which has been fed onto the belt 50b by the feeding unit 50a is supported by the flanges 20f and 20g. In this state, the cassette 20 is transported backward by the moving belt 50b.

When the cassette 20 is detected by the sensor D1s, the methanol inside the receiver 20e is recovered (aspirated) from the receiving hole 20b of the cassette 20 via the recovery pipette D1b of the stain processing unit D1. The smear sample on the slide glass 10 is then dried by a fan not shown in the drawing. The fixing (adhesion) of the smear sample by methanol then ends. Subsequently, May-Grünewald solution is dispensed (discharged) into the receiver 20e of the receiving hole 20b of the cassette 20 via the dispensing pipette D1a. The cassette 20 is then transported backward by the belt 50b.

When the cassette 20 is detected by the sensor D2s, the May-Grünewald solution inside the receiver 20e is recovered (aspirated) from the receiving hole 20b of the cassette 20 via the recovery pipette D2b of the stain processing unit D2. Subsequently, May-Grünewald diluting liquid is dispensed (discharged) into the receiver 20e of the receiving hole 20b of the cassette 20 via the dispensing pipette D2a. The cassette 20 is thereafter transported backward by the belt 50b. Note that the May-Grünewald diluting liquid is a mixture of the May-Grünewald solution of bottle 102 and diluting liquid of bottle 104.

When the cassette 20 is detected by the sensor D3s, the May-Grünewald solution inside the receiver 20e is recovered (aspirated) from the receiving hole 20b of the cassette 20 via the recovery pipette D3b of the stain processing unit D3. Then, Giemsa diluting liquid is dispensed (discharged) into the receiver 20e of the receiving hole 20b of the cassette 20 via the dispensing pipette D3a. The cassette 20 is thereafter transported backward by the belt 50b. Note that the Giemsa diluting liquid is a mixture of the Giemsa solution of bottle 103 and diluting liquid of bottle 104.

When the cassette 20 is detected by the sensor Ws, the Giemsa liquid inside the receiver 20e is recovered (aspirated) from the receiving hole 20b of the cassette 20 via the recovery pipette Wb of the wash processing unit W. Then, water used for sample washing is dispensed (discharged) into the receiver 20e of the receiving hole 20b of the cassette 20 via the dispensing pipette Wa. The water used for sample washing is then recovered (aspirated) from inside the receiver 20e of the cassette 20 by the recovery pipette Wb. The cassette 20 is thereafter transported backward by the belt 50b.

The cassette 20 which has been moved backward by the belt 50b is then sent leftward by the feed unit 50c. The cassette 20 is therefore positioned at the back of the cassette storage unit 51.

The cassette storage unit 51 has a feeding unit 51a and a belt 51b which is movable in a forward direction. The cassette 20 which has been sent from the feed unit 50c is moved onto the belt 51b by the feeding unit 51a. The cassette 20 which has been sent onto the belt 51b is transported forward by the moving belt 51b. The cassette 20 positioned in front of the belt 51b is removed by the user through the opening 2c (refer to FIG. 1). The smear sample preparation therefore ends. Note that the cassette 20 which has been recovered in the cassette storage unit 51 and removed by the user through the opening 2c (refer to FIG. 1), is thereafter again placed in the cassette receiver 47 through the opening 2b (refer to FIG. 1.

The operation of the staining unit 50 (methanol processing unit M, stain processing units D1 through D3, and wash processing unit W) is described next, referring to FIG. 4. Note that the operation of the methanol processing unit M, stain processing units D1 through D3, and wash processing unit W is identical to that of the stain processing unit D1.

FIGS. 4(a) through (c) are side views of the stain processing unit D1 viewed in the Y-axis positive direction. The stain processing unit D1 has, in addition to the dispensing pipette D1a and recovery pipette D1b shown in FIG. 2, a substrate D11, stopper D12, support member D13, and holder D14.

Referring to FIG. 4(a), the substrate D11 is attached within the smear sample preparation device 2. The stopper D12 is a metal plate which is vertically movable (Z-axis direction) relative to the substrate D11, and the sensor D1s is provided on the front surface (surface on the side in the Y-axis negative direction) of the stopper D12. The dispensing pipette D1a, recovery pipette D1b, and holder D14 are integrated with the support member D13 so as to be vertically movable.

In the state shown in FIG. 4(a), the backside surface of the cassette 20, which has been transported backward supported on the belt 50b, abuts the stopper D12 and is stopped. At this time, the cassette 20 is positioned at position D1p of FIG. 2, and the arrival of the cassette 20 is detected by the sensor D1s. In this state, the support member D13 moves downward and the tips of the dispensing pipette D1a and recovery pipette D1b are positioned within the receiver 20e of the cassette 20 as shown in FIG. 4(b).

In the state shown in FIG. 4(b), the methanol within the cassette 20 is recovered by the recovery pipette D1b. The slide glass 10 in the cassette 20 is then gripped by the holder D14 and lifted upward from the cassette 20. In this condition, the slide glass 10 is dried by a fan not shown in the drawing, and thereafter the slide glass 10 is returned into the cassette 20. May-Grünwald solution is then dispensed into the cassette 20 from the dispensing pipette D1a. The support member D13 and the stopper D12 then move upward and in the state shown in FIG. 4(c) the cassette 20 is transported backward by the belt 50b.

Note that the methanol processing unit M has a configuration wherein the stopper D12 of FIG. 4 corresponds to the recovery pipette D1b. In the methanol processing unit M, the slide glass 10, which is accommodated in the cassette 20 positioned at position Mp (refer to FIG. 2), is raised upward by the holder corresponding to the holder D14 of FIG. 4, and thereafter methanol is dispensed to the cassette 20 via the dispensing pipette Ma. The raised slide glass 10 is then returned into the cassette 20. Thereafter, the cassette 20 is fed onto the belt 50b by the feeding unit 50a.

The stain processing unit D2, stain processing unit D3, and wash processing unit W have a structure corresponding to the holder D14 of FIG. 4. In the stain processing unit D2, stain processing unit D3, and wash processing unit W, staining liquid and the like is dispensed and recovered while the slide glass 10 is housed in the cassette 20 respectively positioned at position D2p, D3p, and Wp.

The cassette 20 stored in the cassette storage unit 51 is again placed in the cassette receiver 47. Therefore, when the cassette 20 is used repeatedly, the staining liquid adheres to the cassette 20. In the smear sample preparation device 2 of the present embodiment, the interior of the cassette 20 is washed by dispensing methanol into the cassette 20 in a process separate from the staining process.

In this case, the empty cassette 20 housed in the cassette receiver 47 is transported to the staining unit 50. At position Mp, methanol is dispensed into the cassette 20 by the dispensing pipette Ma, and at position D1p the methanol in the cassette 20 is recovered by the recovery pipette D1p. Hence, the staining liquid adhered within the cassette 20 is washed therefrom.

Note that in the washing process for the interior of the cassette 20 only dispensing of the methanol by the dispensing pipette Ma and the recovery of the methanol by the recovery pipette D1b are performed. That is, the cassette 20 is moved backward without being stopped by the stopper at positions D2p, D3p, and Wp.

In the washing process of the cassette 20, the liquid surface of the methanol dispensed into the cassette 20 by the dispensing pipette Ma is the same height as the liquid surface of the methanol dispensed into the cassette 20 by the dispensing pipette Ma in the staining process. That is, the amount of methanol dispensed for the washing process of the interior of the cassette 20 is a volume just sufficiently greater for the immersion of the slide glass 10 than the amount of methanol dispensed into the cassette 20 in the staining process. Hence, washing is reliably performed since the methanol is in contact with the staining liquid adhering to the interior of the cassette 20 while washing the cassette 20.

FIG. 5 briefly shows a fluid circuit diagram of the smear sample preparation device 2.

The smear sample preparation device 2 has flow passes formed so as to connect the first staining liquid chamber 121, second staining liquid chamber 122, staining liquid chamber 131, diluting liquid chamber 143, first mixing chamber 151, second mixing chamber 152, and discard chamber 165 in addition to the bottles 101 through 104, first methanol chamber 111 and second methanol chamber 112 shown in FIG. 1. Note that although the wash water bottle 105, dispensing pipette Wa, recovery pipette Wb and their corresponding flow passes are illustrated, they are omitted in FIG. 5 for convenience.

As shown in the drawing, valves v11 through v17, v18a, v18b, v19, v20 through v28, v20a, v29b, v30a, v30b, v31 through v34, v35a, v35b, v41a through v43a, v41b through v43b, v51a, v51b, v52a, v52b, and v53 through v56 are connected to the flow pass. The staining liquid and the like is allowed to flow or is blocked via the valves which are set to either an open state or a closed state. Pressure regulators 113 through 115, 123 through 125, 127, 132, 133, 141, 146, 161, 163, 166 for regulating pressure, and diaphragm pumps 116, 126, 128, 134, 142, 145, 147, 162, and 164 which function to aspirate or discharge a set amount of staining liquid or the like are connected to the flow pass as shown in the drawing.

Figure 6:
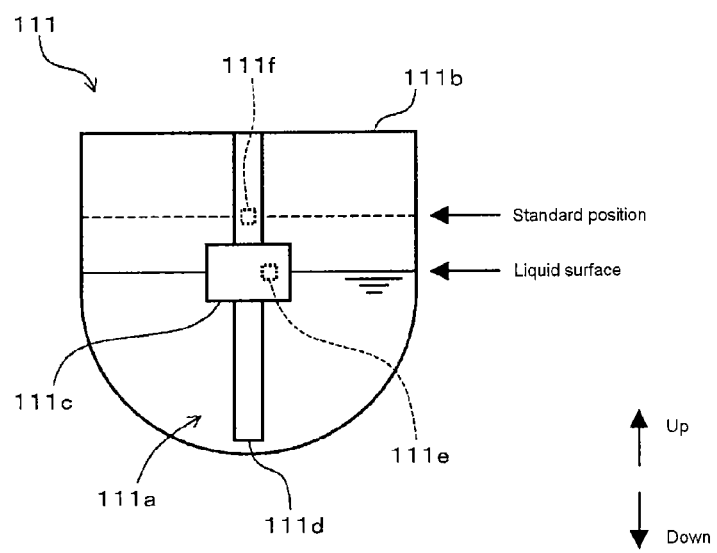
FIG. 6 shows the structure of a first methanol chamber of the embodiment.

Referring to FIG. 6, the first methanol chamber 111 is configured by a tank 111b provided with an internal float switch 111a. The float switch 111a is configured by a float member 111c, and a support rod 111d for supporting the float member 111c so as to be movable in vertical directions. A magnet 111e is embedded within the float member 111c. The float member 111c moves vertically according to the liquid surface within the tank 111b, and the magnet 111e is positioned at the height of the liquid surface. A magnetic sensor type reed switch 111f is embedded at a predetermined position (hereinafter referred to as "standard position") in the vertical direction of the support rod 111d.

The reed switch is turned on when the surface of the liquid within the tank 111b is positioned at the standard position. The reed switch is turned off when the surface of the liquid in the tank 111b is not at the standard position. Hence, it is possible to determine whether a predetermined amount of methanol is retained in the first methanol tank 111.

Note that the second methanol chamber 112, first staining liquid chamber 121, second staining liquid chamber 122, staining liquid chamber 131, diluting liquid chamber 143, and discard chamber 165 have the same structure as the first methanol chamber 111, and are provided with an internal float switch. The standard amount of liquid retained in each chamber, is set individually, and the standard position at which the reed switch is in the turned on state is set individually in accordance therewith.

Returning to FIG. 5, when supplying methanol from the bottle 101 to the first methane chamber 111, the valves v12 through v16 are closed and valve v11 is open. In this state, a vacuum is created within the first methanol chamber 111 by the pressure regulator 113. Hence, the methanol retained in the bottle 101 is supplied into the first methane chamber 111.

When supplying methanol from the bottle 101 to the second methanol chamber 112, the valves v11, v13, v17, and v19 are closed and valve v12 is opened. In this state, there is a vacuum created within the second methanol chamber 112 by the pressure regulator 114. Hence, the methanol retained in the bottle 101 is supplied into the second methane chamber 112.

When the methanol retained in the first methanol chamber 111 is dispensed from the dispensing pipette Ma to the cassette 20, valves v11, v14, v15, v17, and v18b are closed and valves v16 and v18a are opened. In this state, there is a vacuum created within the diaphragm pump 116 by the pressure regulator 115. Hence, a fixed amount of the methanol retained in the first methanol chamber 111 is aspirated into the diaphragm pump 116. Then, the valve v18a is closed and the valve 18b is opened. In this state, a positive pressure is created within the diaphragm pump 116 by the pressure regulator 115. Hence, the methanol within the diaphragm pump 116 is dispensed from the dispensing pipette Ma to the cassette 20.

When the methanol retained in the second methanol chamber 112 is dispensed from the dispensing pipette Ma to the cassette 20, valves v12, v16, v18b, and v19 are closed and valves v17 and v18a are opened. In this state, there is a vacuum created within the diaphragm pump 116 by the pressure regulator 115. Hence, a fixed amount of the methanol retained in the second methanol chamber 112 is aspirated into the diaphragm pump 116. The methanol in the diaphragm pump 116 is then dispensed from the dispensing pipette Ma to the cassette 20 in the same way as the case of the first methanol chamber 111.

When recovering the methanol retained in the cassette 20 in the first methanol chamber 111 via the recovery pipette D1b, the valves v11, v14, v16 are closed and the valve 15 is opened. In this state, a vacuum is created within the first methanol chamber 111 by the pressure regulator 113. Hence, the methanol aspirated from the recovery pipette D1b is recovered in the first methanol chamber 111.

When discharging the methanol retained in the first methanol chamber 111, the valves v11, v15, v16 are closed and the valve v14 is opened. In this state, the pressure is increased within the first methanol chamber 111 by the pressure regulator 113. Hence, the methanol retained in the first methanol chamber 111 is discharged therefrom.

Next, when supplying the May-Grünewald solution as a staining liquid from the bottle 102 to the first staining liquid chamber 121, the valves v22 through v24, v26, and v27 are closed and the valves v20 and v21 are opened. In this state, a vacuum is created within the first staining liquid chamber 121 by the pressure regulator 123. Hence, the May-Grünewald solution retained within the bottle 102 is supplied to the first staining liquid chamber 121.

When supplying May-Grünewald solution from the bottle 102 to the second staining liquid chamber 122, the valves v21, v23, v25, and v28 are closed and the valves v20 and v22 are opened. In this state, a vacuum is created within the second staining liquid chamber 122 by the pressure regulator 124. Hence, the May-Grünewald solution retained within the bottle 102 is supplied to the second staining liquid chamber 122.

When the May-Grünwald solution retained in the first staining liquid chamber 121 is dispensed from the dispensing pipette D1$a$ to the cassette 20, the valves v21, v24, v26, v28, v29$b$, and v30$a$ are closed and the valves v27 and v29$a$ are opened. In this state, there is a vacuum created within the diaphragm pump 126 by the pressure regulator 125. Hence, a fixed amount of the May-Grünewald solution retained in the first staining liquid chamber 121 is aspirated into the diaphragm pump 126. Then, the valve v29$a$ is closed and the valve v29$b$ is opened. In this state, pressure is increased within the diaphragm pump 126 by the pressure regulator 125. Hence, the May-Grünewald solution within the diaphragm pump 126 is dispensed from the dispensing pipette D1$a$ to the cassette 20.

When the May-Grünewald solution retained in the second staining liquid chamber 122 is dispensed from the dispensing pipette D1$a$ to the cassette 20, the valves v22, v25, v27, v28, v29$b$, and v30$a$ are closed and the valves v28 and v29$a$ are opened. In this state, there is a vacuum created within the diaphragm pump 126 by the pressure regulator 125. Hence, a fixed amount of the May-Grünewald solution retained in the second staining liquid chamber 122 is aspirated into the diaphragm pump 126. The May-Grünewald solution in the diaphragm pump 126 is then dispensed from the dispensing pipette D1$a$ to the cassette 20 in the same way as the case of the first staining liquid chamber 121.

When recovering the May-Grünewald solution retained in the cassette 20 in the first staining liquid Chamber 121 via the recovery pipette D2$b$, the valves v21, v24, v27 are closed and the valve v26 is opened. In this state, a vacuum is created within the first staining liquid chamber 121 by the pressure regulator 123. Hence, the May-Grünewald solution aspirated from the recovery pipette D2$b$ is recovered in the first staining liquid chamber 121.

When supplying the May-Grünewald solution retained in the first staining liquid chamber 121 to the first mixing chamber 151, the valves v21, v24, v26, v28, v29$a$, and v30$b$ are closed and the valves v27 and v30$a$ are opened. In this state, there is a vacuum created within the diaphragm pump 128 by the pressure regulator 127. Hence, a fixed amount of the May-Grünewald solution retained in the first staining liquid chamber 121 is aspirated into the diaphragm pump 128. Then, the valve v30$a$ is closed and the valve v30$b$ is opened. In this state, pressure is increased within the diaphragm pump 128 by the pressure regulator 127. In this way the May-Grünewald solution within the diaphragm pump 128 is supplied to the first mixing chamber 151. Note that an opening is provided in the first mixing chamber 151 to equalize the pressure within the chamber with the ambient pressure outside.

When supplying the May-Grünewald solution retained in the second staining liquid chamber 122 to the first mixing chamber 151, the valves v22, v25, v27, v29$a$, and v30$b$ are closed and the valves v28 and v30$a$ are opened. In this state, there is a vacuum created within the diaphragm pump 128 by the pressure regulator 127. Hence, a fixed amount of the May-Grünewald solution retained in the second staining liquid chamber 122 is aspirated into the diaphragm pump 128. The May-Grünewald solution in the diaphragm pump 128 is then supplied to the first mixing chamber 151 in the same way as the case of the first staining liquid chamber 121.

When discharging the May-Grünewald solution retained in the first staining liquid chamber 121, the valves v21, and v25 through v27 are closed and the valve v24 is opened. In this state, the pressure is increased within the first staining liquid chamber 121 by the pressure regulator 123. Hence, the May-Grünewald solution retained in the first staining liquid chamber 121 is discharged.

When discharging the May-Grünewald solution retained in the second staining liquid chamber 122, the valves v22, v24 and v28 are closed and the valve v25 is opened. In this state, the pressure is increased within the second staining liquid chamber 122 by the pressure regulator 124. Hence, the May-Grünewald solution retained in the second staining liquid chamber 122 is discharged.

Similarly, by controlling the corresponding valves, pressure regulator and diaphragm pump, the Giemsa solution (staining liquid) is supplied from the bottle 103 to the staining solution chamber 131 Giemsa solution retained in the staining liquid chamber 131 is supplied to the second staining chamber 152, phosphate buffer solution (diluting liquid) is supplied from the bottle 104 to the diluting liquid chamber 143, diluting liquid retained in the diluting liquid chamber 143 is supplied to the first mixing chamber 151, and diluting liquid retained in the diluting liquid chamber 143 is supplied to the second mixing chamber 152.

In the first mixing chamber 151, the May-Grünewald solution supplied from the first staining liquid chamber 121 or the second staining liquid chamber 122 is mixed with the diluting liquid supplied from the diluting liquid chamber 143. Hence, a May-Grünwald dilute solution is produced within the first mixing chamber 151. In the second mixing chamber 152, the Giemsa solution supplied from the staining liquid chamber is mixed with the diluting liquid supplied from the diluting liquid chamber 143. Hence, a Giemsa dilute solution is produced within the second mixing chamber 152.

By controlling the corresponding valves, pressure regulator and diaphragm pump, the Giemsa solution retained in the staining liquid chamber 131 is dispensed from the dispensing pipette D2$a$ to the cassette 20, and Giemsa dilute solution retained in the second mixing chamber 152 is dispensed from the dispensing pipette D3$a$ to the cassette 20. The May-Grünewald dilute solution retained in the cassette 20 is recovered in the discard chamber 165 via the recovery pipette D3$b$, the May-Grünewald dilute solution retained in the first mixing chamber 151 is supplied to the discard chamber 165, and the Giemsa dilute solution retained in the second mixing chamber 152 is supplied to the discard chamber 165. The staining solution and the like retained in the discard chamber 165 is discharged therefrom by controlling the valves v53 through v56 and the pressure regulator 166.

Note that the Giemsa dilute solution retained in the cassette 20 is recovered similar to the above through the recovery pipette Wb via chamber, diaphragm pump, and valves not shown in the drawings. The washing water retained in the bottle 105 is similarly dispensed to the cassette 20 through the dispensing pipette Wa and recovered through the recovery pipette Wb via chamber, diaphragm pump, and valves not shown in the drawing.

Thus, the staining liquid and the like accommodated in the bottles 101 through 105 can be dispensed to the cassette 20 through the flow pass by the dispensing pipettes Ma, D1$a$ through D3$a$, and Wa. The staining liquid and the like aspirated by the recovery pipettes Wb and D1$b$ through D3$b$ can be recovered in the corresponding chambers through the flow pass. The staining liquid and the like retained in each chamber also can be discharged through the flow pass.

Figure 7:
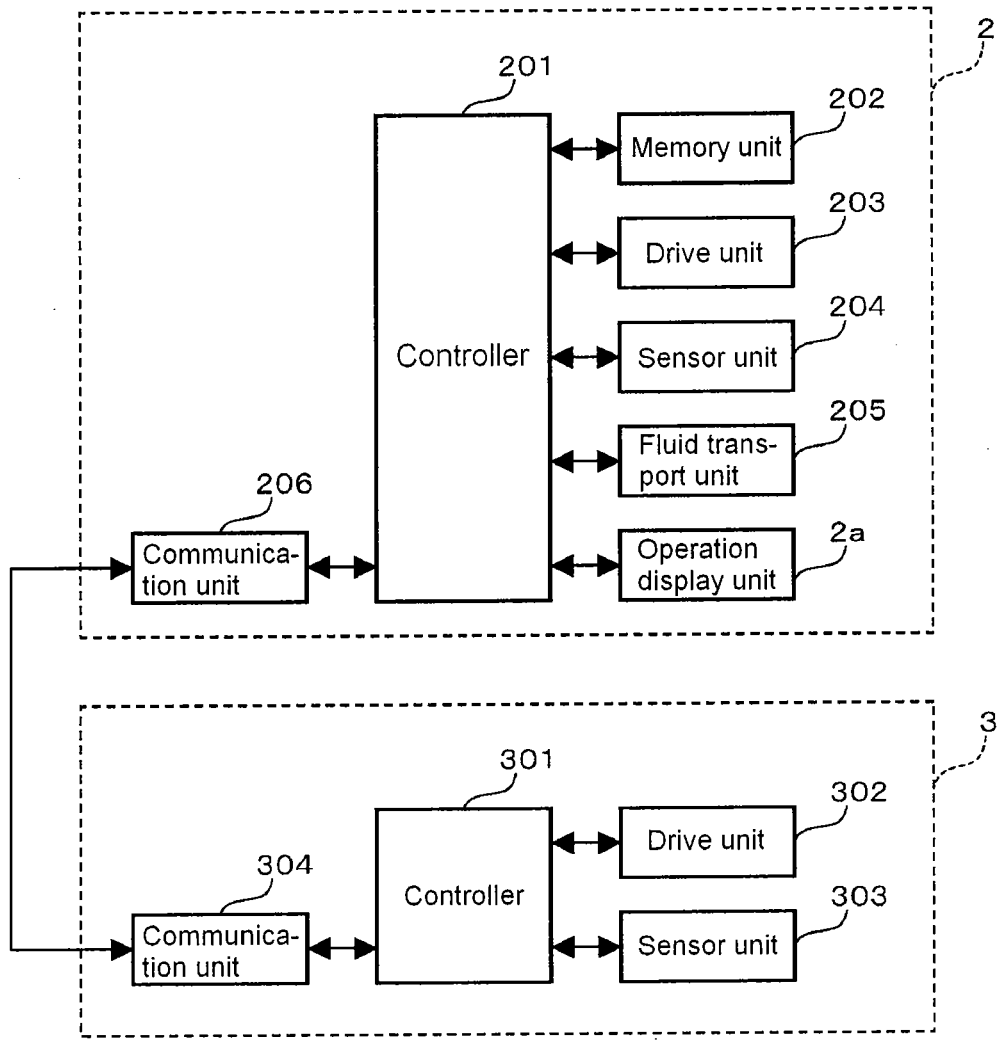
FIG. 7 briefly shows the structures of a transport device and the smear preparation apparatus of the embodiment.

FIG. 7 briefly shows a the structures of the smear sample preparation device 2 and the transport device 3.

The smear sample preparation device 2 is provided with a controller 201, memory unit 202, drive unit 203, sensor unit 204, fluid transporter 205, communication unit 206, and operation display unit 2a.

The controller 201 controls the parts of the smear sample preparation device 2 by executing a computer program stored in the memory unit 202. The memory unit 202 is a memory device such as a hard disk and the like, and stores a computer program for operating the smear sample preparation device 2.

The memory unit 202 stores a reuse counter Rk for indicating the frequency of methanol reuse, a threshold frequency R0 for indicating the upper limit reuse frequency, a recovery counter Ck for indicating the methanol recovery frequency, and a threshold frequency C0 for indicating the upper limit of the recovery frequency, which will be described later. These frequencies are described later with reference to FIGS. 10(b), 12(b), and 14.

The drive unit 203 includes an aspirating/dispensing mechanism 41, slide glass supplier 42, slide glass cross-feeder 43, smearing mechanism 44, smear drier 45, printer 46, cassette receiver 47, cassette cross-feeder 48, cassette rotator 49, staining unit 50, and cassette storage unit 51, and a mechanism for driving each part within the smear sample preparation device 2, and is controlled by the controller 201.

The sensor unit 204 includes a sensor Ms for the methanol processing unit M, sensors D1s through D3s for the stain processing units D1 through D3, and sensor Ws for the wash processing unit W. The sensor unit 204 includes a reed switch 111f for the first methanol chamber 111, and similar reed switches disposed in the other chambers. Each sensor included in the sensor unit 204 is controlled by the controller 201, and the detection signals of the sensor unit 204 are output to the controller 201.

The liquid transporter 205 includes pressure regulators 113 through 115, 123 through 125, 127, 132, 133, 141, 144, 146, 161, 163, 166, and valves v11 through v17, v18a, v18b, v10, v20 through v28, v29a, v29b, v30a, v30b, v31 through v34, v35a, v35b, v41a through v43a, v41b through v43b, v51a, v51b, v52a, v53b, v53 through v56. The parts included in the liquid transporter 205 are controlled by the controller 201.

The operation display unit 2a is a touch panel with integrated input and display functions, as shown in FIG. 1. When the user operates the operation display unit 2a, a signal indicting the operation content is output to the controller 201. The controller 201 displays each type of information on the operation display unit 2a. The communication unit 206 performs data communication with the communication unit 304 of the transport device 3.

The transport device 3 is provided with a controller 301, drive unit 302, sensor unit 303, and communication unit 304. The controller 301 controls the parts within the transport device 3. The drive unit 302 includes mechanism for driving each part in the transport device 3, and is controlled by the controller 301. The sensor unit 303 includes sensors in the transport device 3, is controlled by the controller 301, and the detection signal of the sensor unit 303 is output to the controller 301. The communication unit 304 performs data communication with the communication unit 206 of the smear sample preparation device 2.

Figure 8:
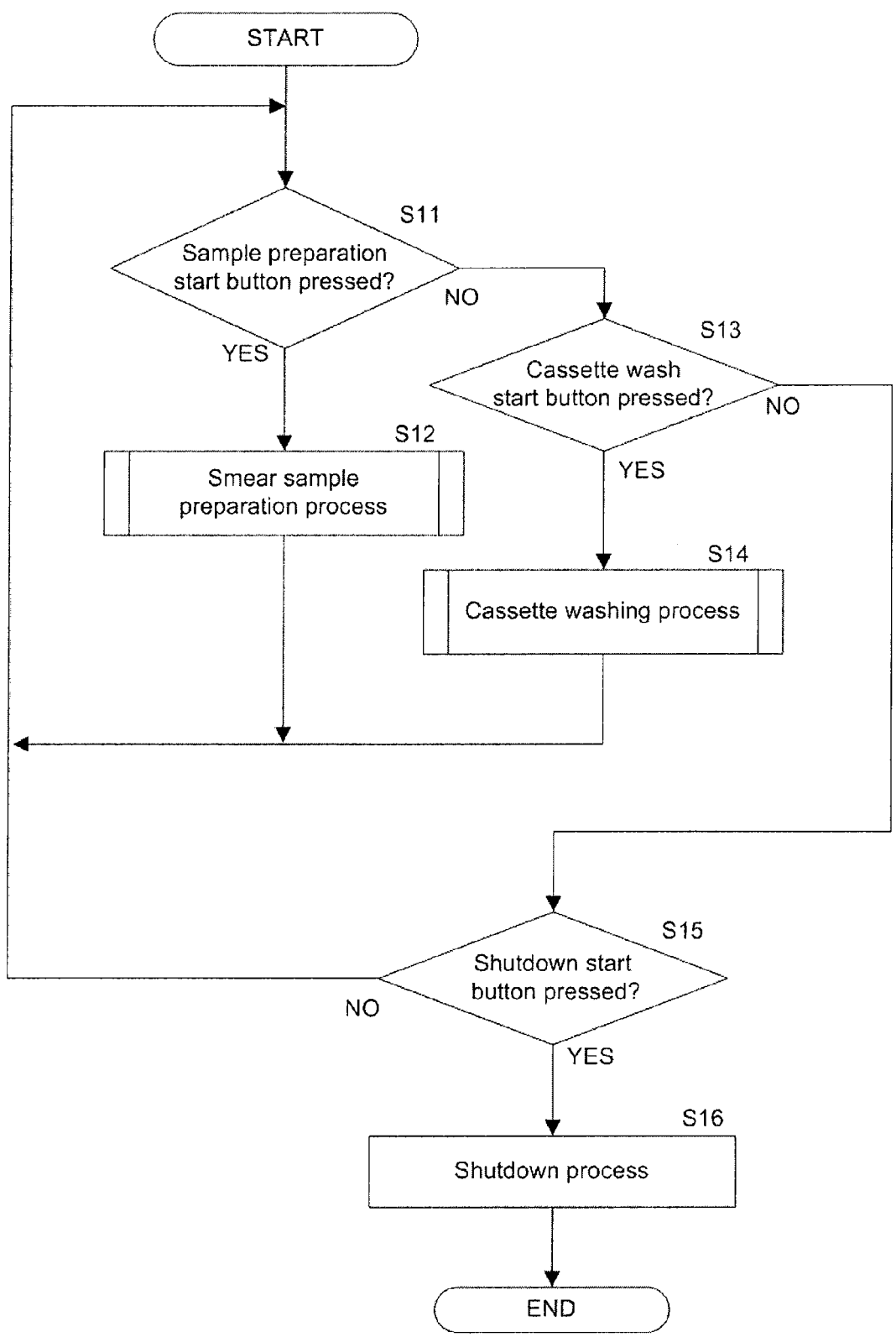
FIG. 8 is a flow chart showing the processes of the smear preparation apparatus of the embodiment.

FIG. 8 is a flow chart showing the processes of the smear sample preparation device 2.

The controller 201 executes processes corresponding to the pressed button when the user presses any of the buttons including the smear sample preparation start button 401, cassette washing start button 402, or shutdown start button 501.

Figure 9A:
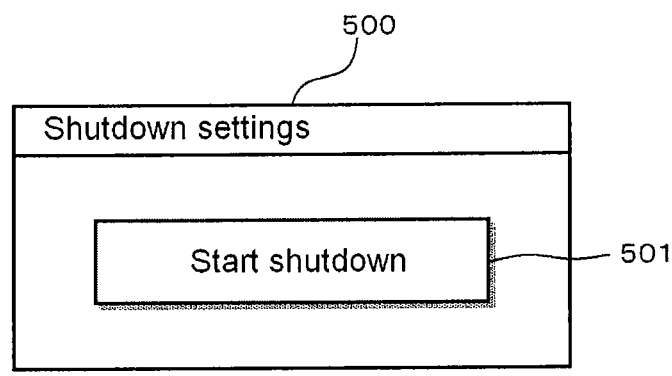
FIGS. 9(a) and 9(b) show a start setting screen and a shutdown setting screen of the embodiment.
Figure 9B:
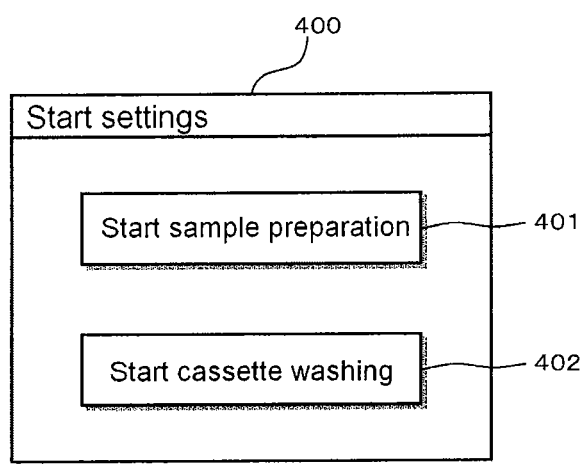

FIG. 9(a) shows the start setting screen 400 displayed on the operation display 2a. The smear sample preparation start button 401 and the cassette washing start button 402 are displayed on the start setting screen 400. FIG. 9(b) shows the shutdown setting screen 500 displayed on the operation display 2a. The shutdown start button 501 is displayed on the shutdown start setting screen 500. Note that the user can suitably display the start setting screen 400 and the shutdown setting screen 500 by operating the operation display unit 2a.

Returning to FIG. 8, when the controller 201 determines that the smear sample preparation start button 401 has been pressed (step S11: YES), the smear sample preparation process is executed (S12). When the controller 201 determines that the cassette washing start button 402 has been pressed (step S12: N0, S13: YES), the cassette washing process is executed (S12). When the controller 201 determines that the shutdown start button 501 has been pressed (S11: N0, S13: N0, S15: YES), the shutdown process is executed for the smear sample preparation device 2. The smear sample preparation process and the cassette washing process are described below referring to FIGS. 10(a) and 12(a). Note that the controller 201 displays the message "Smear sample preparation process is executing" is displayed on the operation display unit 2a while the smear sample preparation process (S12) is being performed. On the other hand, that the controller 201 displays the message "Cassette washing process is executing" is displayed on the operation display unit 2a while the cassette washing process (S14) is being performed. Hence, the operator and others can readily comprehend whether the device is currently performing a process by confirming the indication on the operation display unit 2a of the smear sample preparation device 2.

Selection of the cassette wash start button 402 is disabled while the smear sample preparation process (S12) is being performed after selecting the smear sample preparation start button 401. On the other hand, selection of the smear sample preparation start button 401 is disabled while the cassette washing process (S14) is being performed after selecting the cassette wash start button 402. Thus, mixing of washed cassettes 20 and cassettes 20 with adhered staining liquid in the cassette storage unit 51 can be prevented by not interrupting an ongoing process with another process. Suspending a process through operation error also is prevented.

Figure 10A:
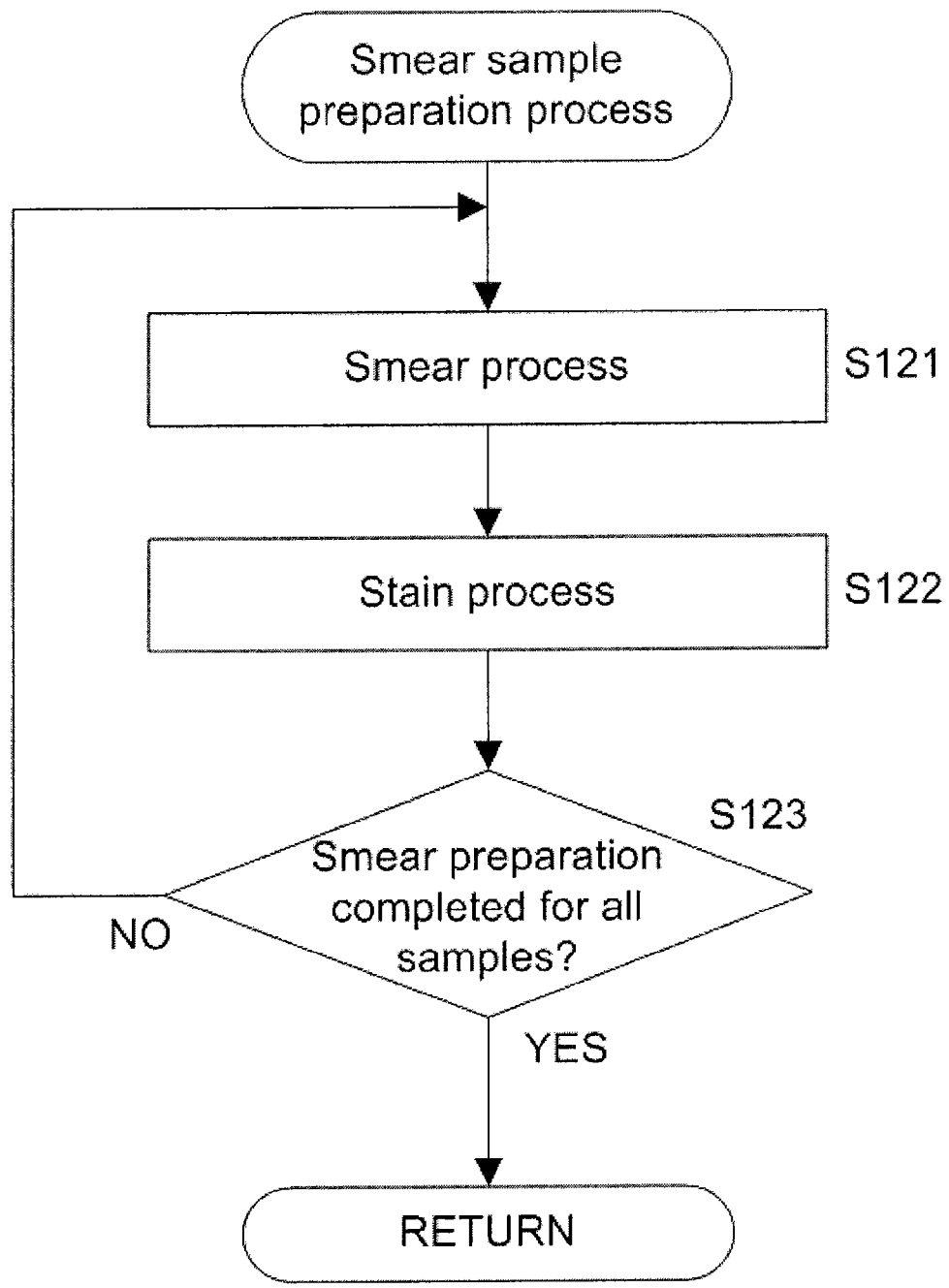
FIGS. 10(a) and 10(b) are flow charts showing the methanol dispensing process in the staining process and smear preparation process of the embodiment.

FIG. 10(a) is a flow chart showing the smear sample preparation process.

The controller 201 aspirates the sample positioned in front of the hand unit 41a (refer to FIG. 1) and performs the smear process (S121). That is, the controller 201 prepares a smear sample from the aspirated sample, houses the smear sample in the cassette 20, and positions the cassette 20 at the position Mp. The controller 201 then performs the staining process on the cassette 20 positioned at the position Mp via the staining unit 50, and transports the cassette 20 to the cassette storage unit 51.

The controller 201 then determines whether the smear preparation (S121, S122) has been completed for all samples (S123). When smear preparation of all samples is not complete (S123: NO), the controller 201 returns the process to S121, and sequentially performs smear preparation for subsequent samples. When smear preparation for all samples is completed (S123: YES), the smear sample preparation process ends.

In the staining process of the present embodiment, methanol, which has been dispensed from the first methanol chamber 111 to the cassette 20 through the dispensing pipette Ma, is then recovered in the first methanol chamber 111 through the recovery pipette D1b, and reused for dispensing through the dispensing pipette Ma.

Figure 10B:
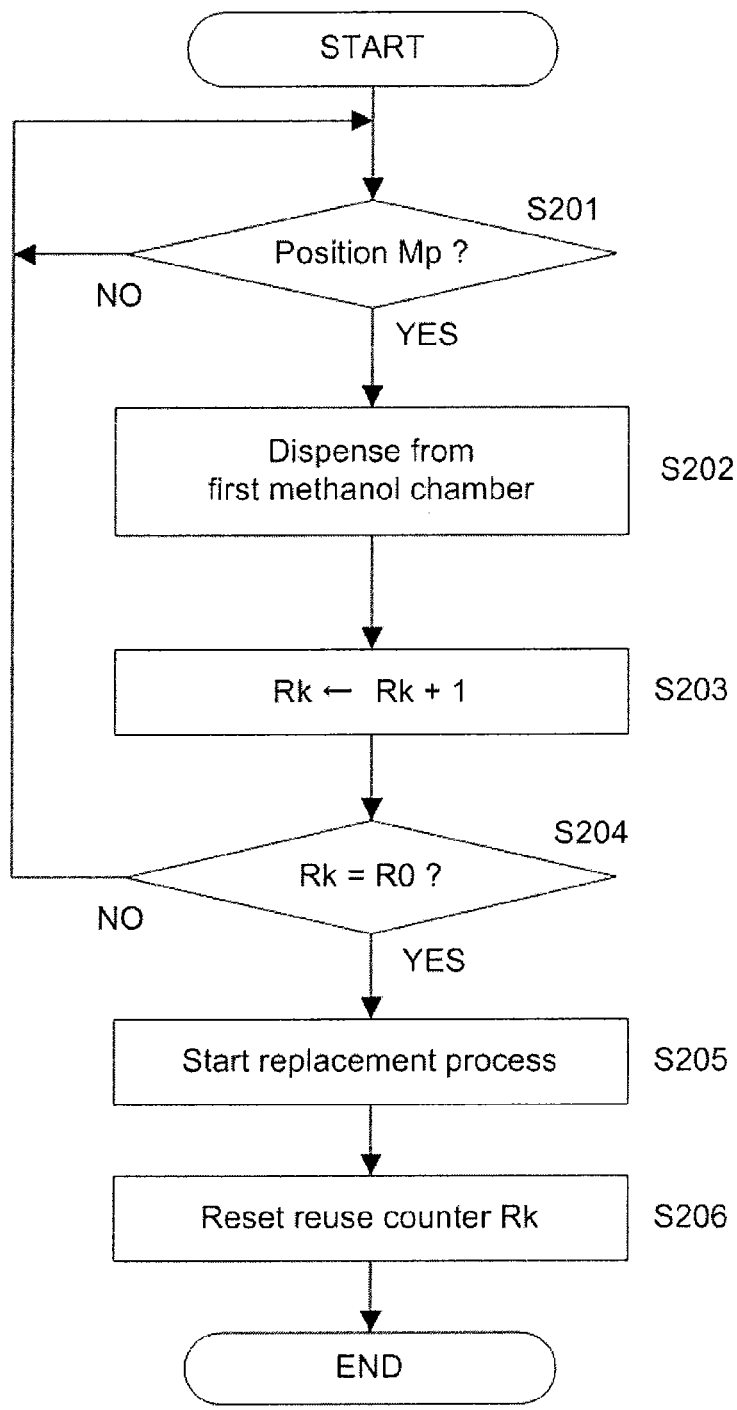

FIG. 10(b) is a flow chart showing the methanol dispensing process in the staining process of the present embodiment.

When the dispensing process starts, the controller 201 awaits the arrival of the cassette 20 at the position Mp. When the cassette 20 arrives at the position Mp (S201: YES), the controller 201 dispenses methanol from the first methanol chamber 111 to the cassette 20 (S202), and adds [1] to the reuse counter Rk (S203). The reuse counter Rk is stored in the memory unit 202 and is reset during initial startup of the smear sample preparation device 2. The controller 201 then determines whether the reuse counter Rk has attained a preset threshold frequency R0 (S204). The threshold frequency R0 is stored in the memory unit 202.

Figure 13A:
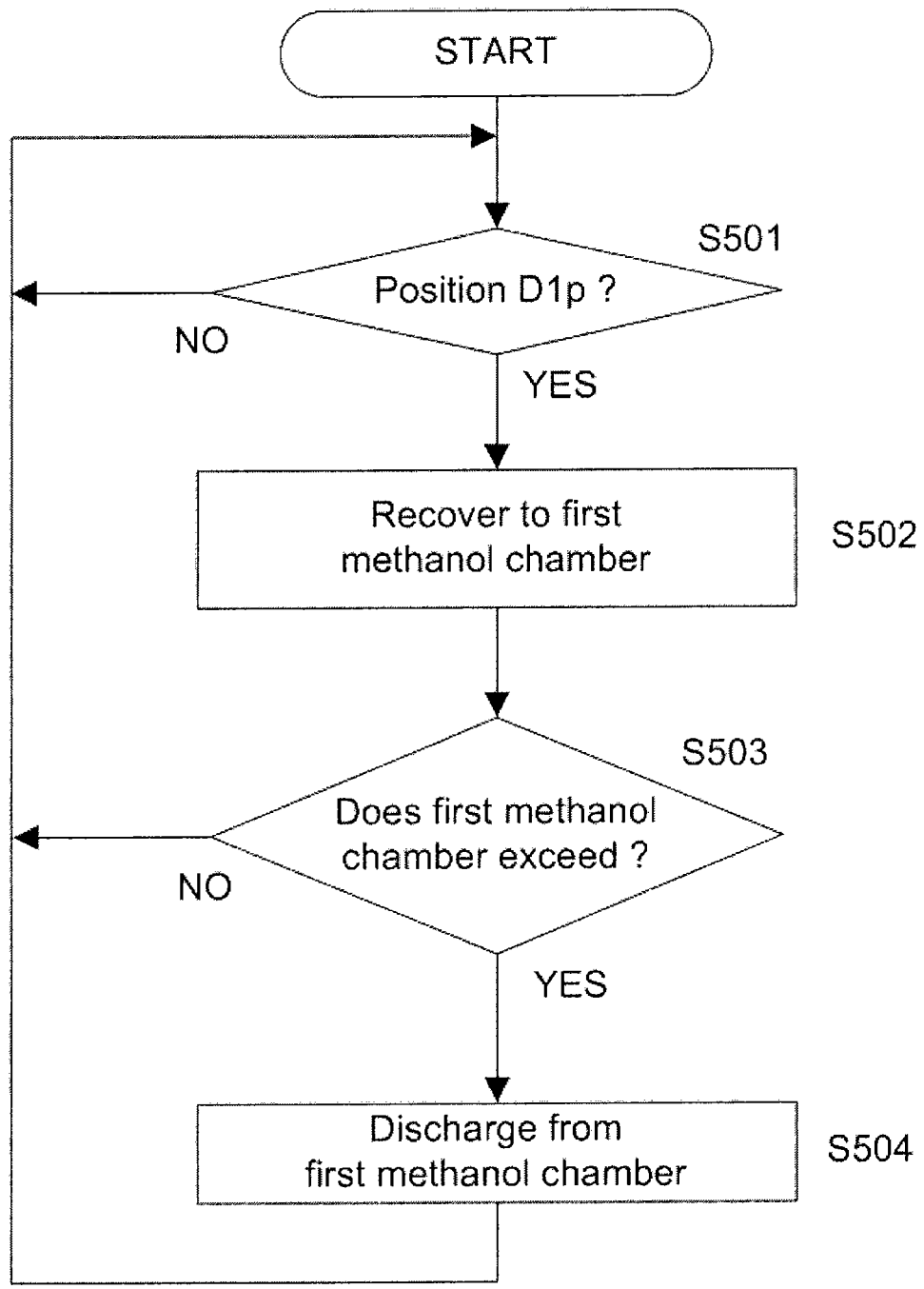
FIGS. 13(a) and 13(b) are flow charts of the methanol collection process and the counting process of the collection counter of the embodiment.

Note that the methanol dispensed to the cassette 20 is recovered from the cassette 20 to the first methanol chamber 111 at the position D1p. Therefore, as the dispensing process progresses, the methanol in the first methanol chamber 111 is gradually degraded. The methanol recovery process is described below referring to FIG. 13(a).

When the reuse counter Rk has not attained the threshold frequency R0 (S204: NO), the controller 201 returns the process to S201, and the process of S201 and subsequent steps are repeated. Therefore, the methanol is dispensed from the first methanol chamber 111 to the cassette 20 until the reuse counter Rk reaches the threshold frequency R0. In the present embodiment, the threshold frequency R0 is user settable. The threshold frequency R0 is an indicator to replace the methanol in the first methanol chamber 111 with fresh methanol.

Figure 11A:
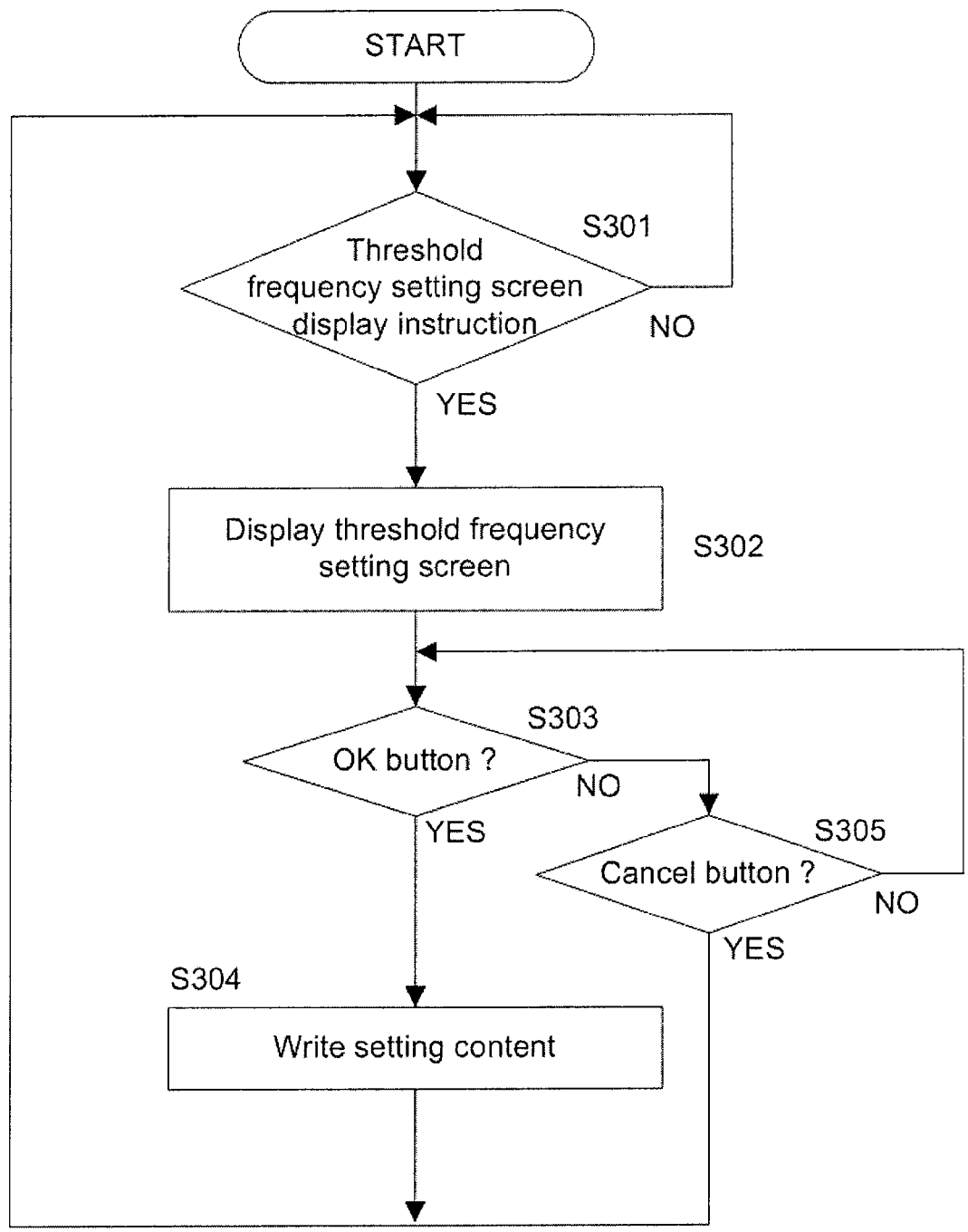
FIGS. 11(a) and 11(b) show threshold number setting screen and a flow chart of the threshold number setting process of the embodiment.

FIG. 11(a) is a flow chart showing the process for setting the threshold frequency R0.

When the controller 201 receives a display instruction of the threshold frequency setting screen 600 from the user (S301: YES), the controller 201 displays the threshold frequency setting screen 600 on the operation display unit 2a (S302) (refer to FIG. 1).

Figure 11B:
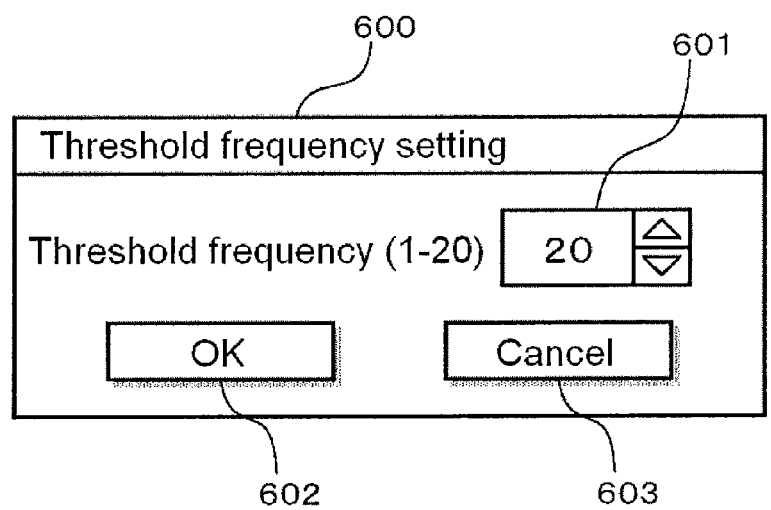

FIG. 11(b) shows the threshold frequency setting screen 600 displayed on the operation display unit 2a. The threshold frequency setting screen 600 has an input field 601, OK button 602, and cancel button 603. The input field 601 is an area capable of receiving numbers 1 to 20 input by the user. The input field 601 includes up and down buttons; when the user presses the up button, the number in the input field 601 is incremented, whereas the number in the input field 601 is decremented when the down button is pressed. Note that the number 20 is set as the default value in the threshold frequency R0.

When the user presses the OK button 602 (S303: YES), the controller 201 writes the numerical value entered in the input field 601 in the threshold frequency R0 stored in the memory unit 202 (S304) and the threshold frequency setting screen 600 closes; when the cancel button 603 is pressed (S303: NO, S305: YES), the value entered in the input field 601 is deleted and the threshold frequency setting screen 600 closes.

Returning to FIG. 10(b), when the reuse counter Rk attains the threshold frequency R0 (S204: YES), the controller 201 starts, in parallel with the dispensing process, a process for replacing the methanol in the first methanol chamber 111 with fresh methanol (S205). When the replacement process of the first methanol chamber 111 ends, the controller 201 resets the reuse counter Rk (S206) and returns the process to S201. Thus, a new dispensing process starts after the methanol replacement.

Figure 12A:
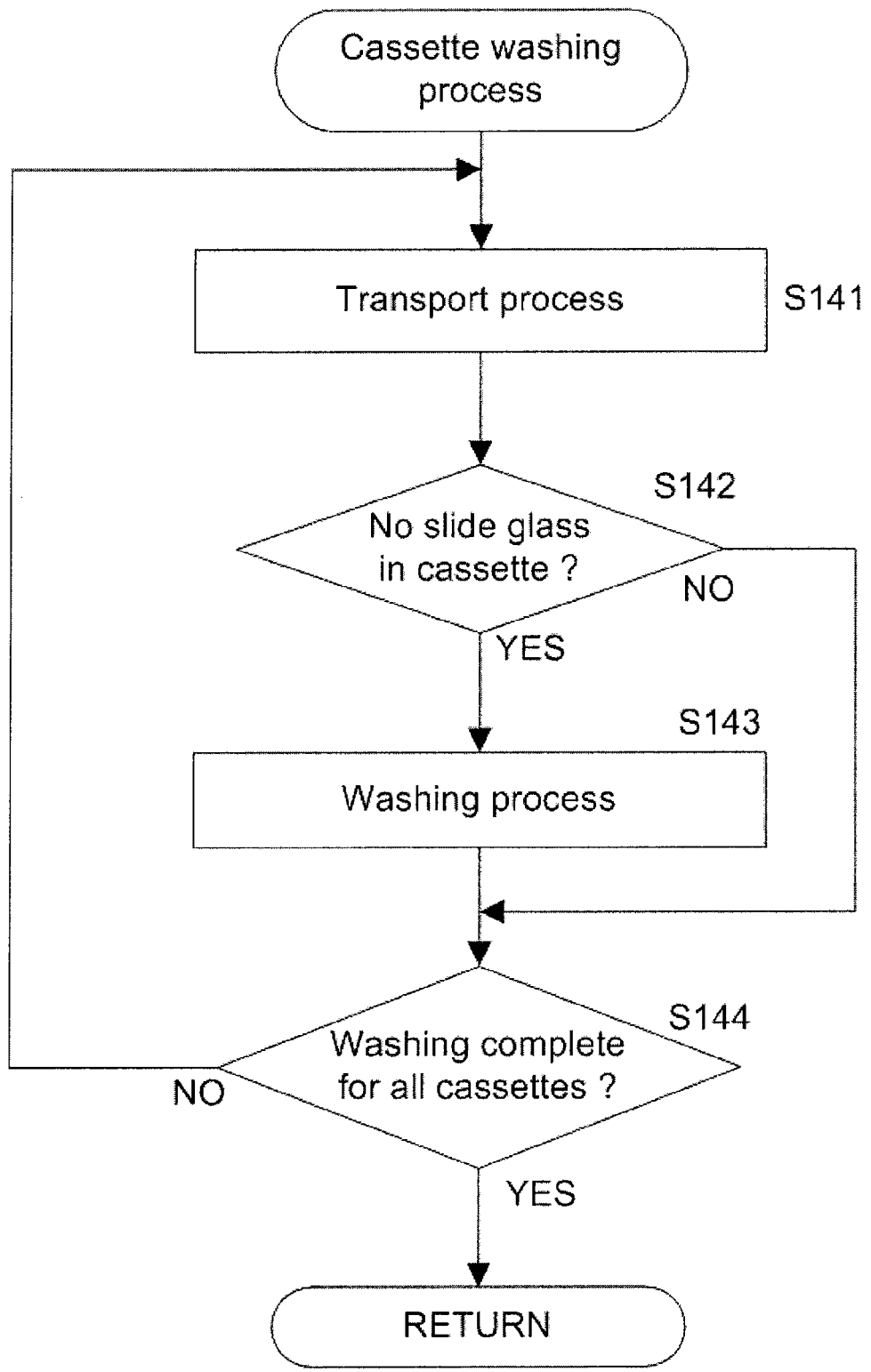
FIGS. 12(a) and 12(b) are flow charts of the cassette washing process and a flow chart of the methanol dispensing process in the washing process of the embodiment.

FIG. 12(a) is a flow chart showing the cassette washing process.

When the cassette wash start button 402 of FIG. 9 is pressed, the controller 201 transports the cassette 20 held in the cassette receiver 47 toward the cassette storage unit 51 (S141). At this time, the cassette 20 held in the cassette receiver 47 is transported forward by the belt 47a and supported by the cassette support 48a of the cassette cross-feeder 48. The cassette 20 supported on the cassette support 48a is positioned in front of the cassette rotator 49. Here, the controller 201 determines whether a slide glass 10 is accommodated in the cassette 20 via the sensor 48s (S142).

When the cassette 20 does not contain a slide glass 10 (S142: YES), the controller 201 performs the washing process on the cassette 20 (S143). That is, methanol is dispensed by the dispensing pipette Ma to the cassette 20 positioned at position Mp, and methanol is recovered by the recovery pipette D1b from the cassette 20 positioned at the position D1p as previously described. After the washing process ends, the washed cassette 20 is transported to the cassette storage unit 51. When the cassette 20 contains a slide glass 10 (S142: NO), the washing process is not performed, and the cassette 20 is moved backward by the belt 50b of the staining unit 50 to the cassette storage unit 51.

The controller 201 then determines whether washing (S141 through S143) has been completed for all cassettes 20 (S144). This determination is YES if a cassette 20 is detected by the sensor 47, and this determination is NO is a cassette 20 is not detected. When washing of all cassettes 20 is not complete (S144: NO), the controller 201 returns the process to S141, and sequentially performs washing for subsequent cassettes 20. When washing of all cassettes 20 is completed (S144: YES), the cassette washing process ends.

In the washing process of the present embodiment, methanol, which has been dispensed from the first methanol chamber 111 to the cassette 20 through the dispensing pipette Ma, is then recovered in the first methanol chamber 111 through the recovery pipette D1b, and reused for dispensing through the dispensing pipette Ma similar to the smear sample preparation process.

Figure 12B:
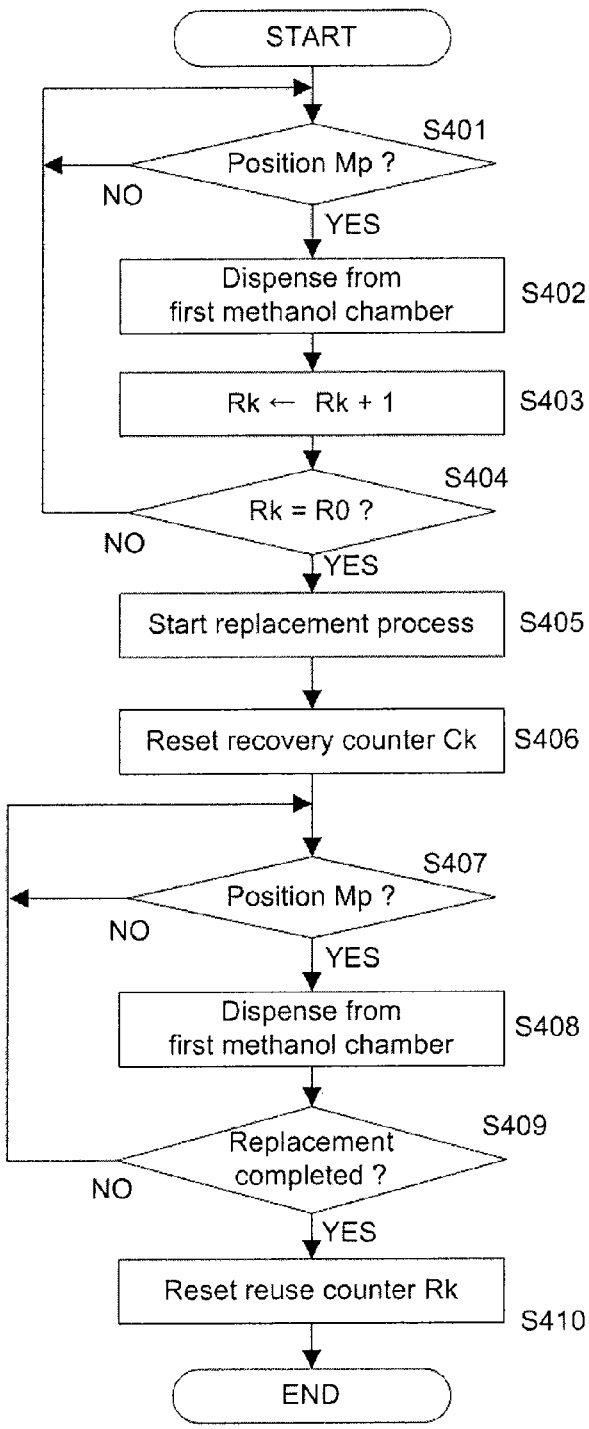

FIG. 12(b) is a flow chart showing the methanol dispensing process in the washing process of the present embodiment.

When the dispensing process starts, the controller 201 awaits the arrival of the cassette 20 at the position Mp. When the cassette 20 arrives at the position Mp (S401: YES), the controller 201 dispenses methanol from the first methanol chamber 111 to the cassette 20 (S402), and adds [1] to the reuse counter Rk (S403). Note that when the cassette 20 washing operation started after the staining operation, the incrementation by S403 was made on the reuse counter Rk incremented in S403 of FIG. 10b). The controller 201 then determines whether the reuse counter Rk has attained a preset threshold frequency R0 (S204). The reuse counter Rk and the threshold frequency R0 are the same as the Rk and R0 used in the dispensing process of the staining process of FIG. 10(b).

Note that, in this case also, the methanol dispensed to the cassette 20 is recovered from the cassette 20 to the first methanol chamber 111 at the position D1p. Therefore, as the dispensing process progresses, the methanol in the first methanol chamber 111 is gradually degraded. Recovery of the methanol is performed according to the recovery process of FIG. 13(a).

When the reuse counter Rk has not attained the threshold frequency R0 (S404: NO), the controller 201 returns the process to S401, and the process of S401 and subsequent steps are repeated. Therefore, the methanol is dispensed from the first methanol chamber 111 to the cassette 20 until the reuse counter Rk reaches the threshold frequency R0.

When the reuse counter Rk attains the threshold frequency R0 (S404: YES), the controller 201 starts, in parallel with the dispensing process, a process for replacing the methanol in the first methanol chamber 111 with fresh methanol (S405), and starts the count of the recovery counter Ck (S406). The recovery counter Ck is stored in the memory unit 202. The methanol recovery process is described below referring to FIG. 14. The counting process of the recovery counter Ck is described below referring to FIG. 13(*b*).

Thereafter, the controller 201 awaits the arrival of the cassette 20 at the position Mp (S407). When the cassette 20 arrives at the position Mp (S407: YES), the controller 201 dispenses methanol to the cassette 20 from the second methanol chamber 112 rather than from the first methanol chamber 111. Hence, when the methanol replacement process starts, the methanol chamber used to dispense methanol to the cassette 20 is switched from the first methanol chamber 111 to the second methanol chamber 112.

It is then determined whether the methanol replacement in the first methanol chamber 111 is complete (S409). When the methanol replacement in the first methanol chamber 111 is not complete (S409: NO), the controller 201 returns the process to S407. Hence, the methanol is dispensed from the second methanol chamber 112 to the cassette 20 until the methanol replacement in the first methanol chamber 111 is completed. Note that the recovery process of FIG. 13(*a*) is performed and the methanol from the cassette 20 is recovered to the first methanol chamber 111 even when methanol is dispensed from the second methanol chamber 112. When the methanol replacement in the first methanol chamber 111 is completed (S409: YES), the controller 201 resets the reuse counter Rk (S410), and returns the process to S401. Thus, a new dispensing process starts after the methanol replacement.

Figure 13B:
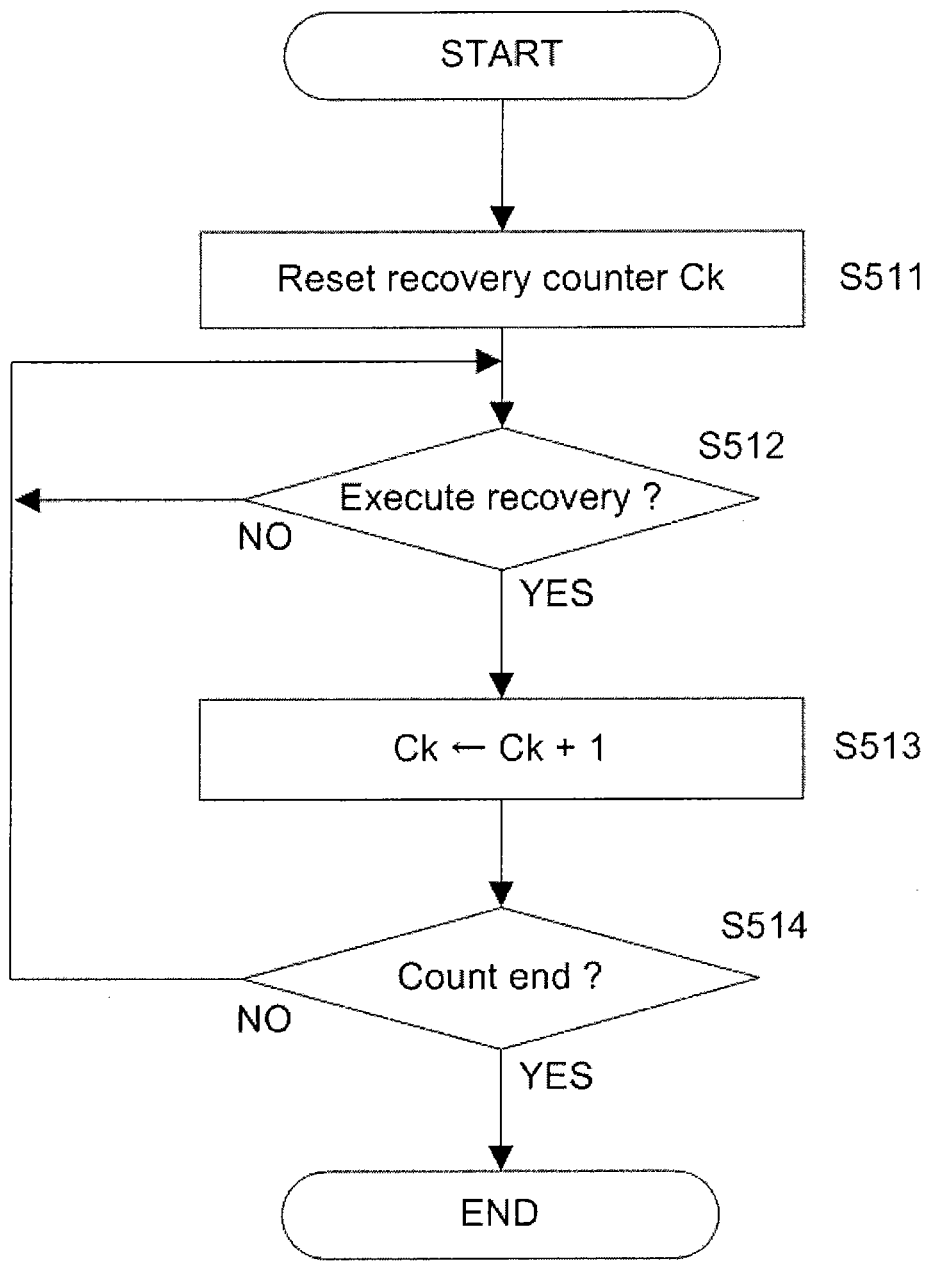

FIG. 13(*a*) is a flow chart showing the methanol recovery process.

The controller 201 awaits the arrival of the cassette 20 at the position D1*p* (S501). When the cassette 20 arrives at the position D1*p* (S501: YES), the controller 201 recovers the methanol from the cassette 20 to the first methanol chamber 111 (S502). Then, the controller 201 determines whether the liquid surface of the first methanol chamber exceeds the standard position (S503); when the liquid surface exceeds the standard position (S503: YES), the methanol is discharged from the first methanol chamber 111 until the liquid surface in the first methanol chamber 111 is at the standard position (S504). Thereafter, the controller 201 returns to S501 and awaits the arrival of the next cassette 20 at the position Dp1. Hence, methanol dispensed to the cassette 20 is recovered in the first methanol chamber 111. The methanol in the second methanol chamber 112 is therefore maintained in a fresh unused condition.

FIG. 13(*b*) is a flow chart showing the count process of the recover counter Ck.

When the recovery counter Ck count process starts in S406 of FIG. 12(*b*), the controller 201 resets the recovery counter Ck (S511). When recovering the methanol from the cassette 20 in the first methanol chamber 111 via the process of FIG. 13(*a*), the controller 201 adds [1] to the recovery counter Ck (S513). The counting process is performed until the recovery counter Ck count process is canceled. Cancellation of the recovery counter Ck counting process is performed in S602 of FIG. 14.

Figure 14:
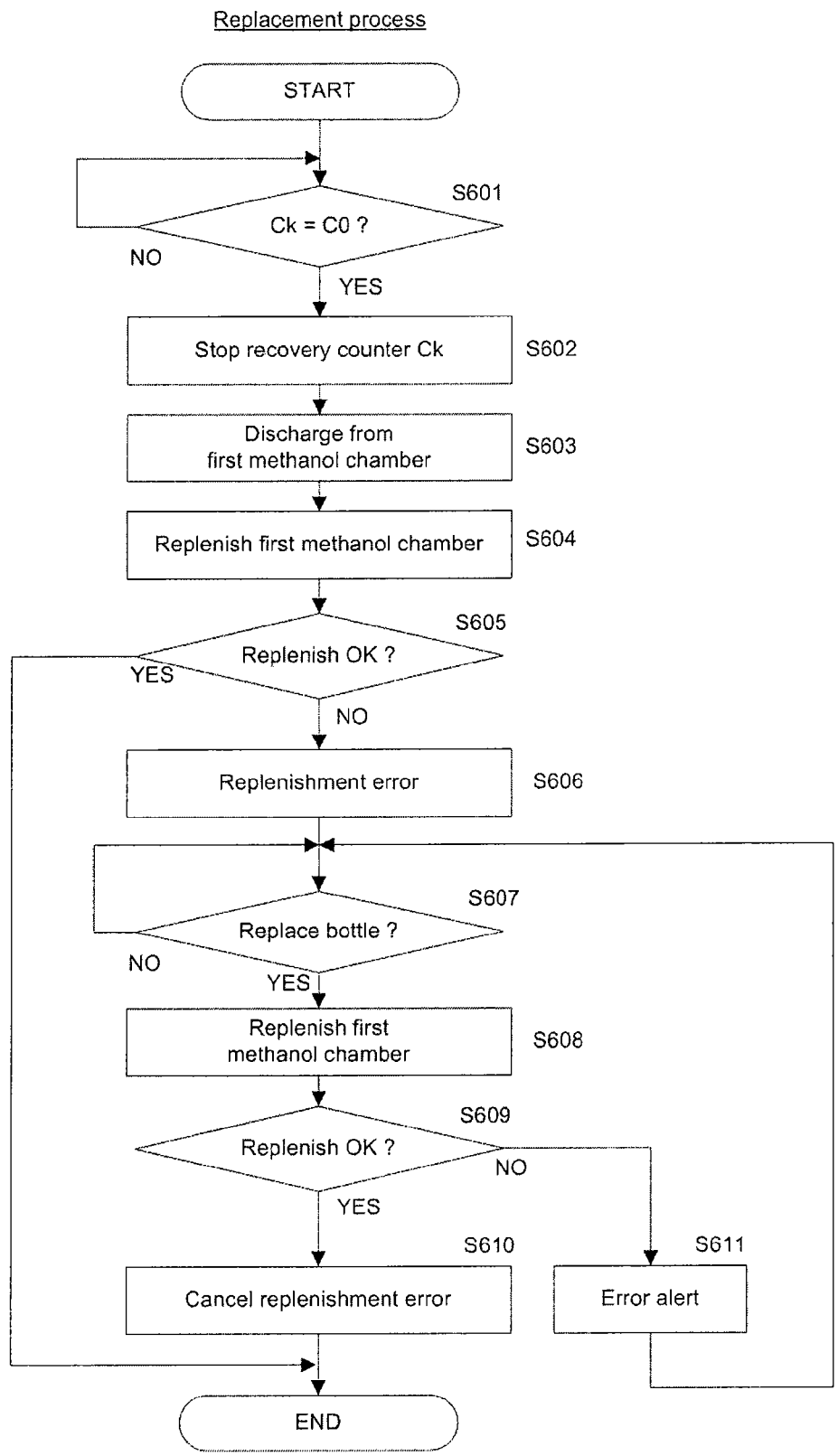
FIG. 14 is a flow chart of the methanol replacement process of the first methanol chamber of the embodiment.

FIG. 14 is a flow chart showing the methanol replacement process of the first methanol chamber 111.

When the methanol replacement process starts in S405 of FIG. 12, the controller 201 waits for the recovery counter Ck to attain the threshold frequency C0 (S601). The threshold frequency C0 is a value pre-stored in the memory unit 202. When the recovery counter Ck attains the threshold frequency C0 (S601: YES), the controller 201 cancels the count of the recovery counter Ck (S602), discharges all methanol in the first methanol chamber 111 (S603), and thereafter replenishes fresh methanol from the bottle 101 to the first methanol chamber 111 (S604). Hence, the replacement process ends when the methanol is replenished in the first methanol chamber 111 until the liquid surface attains the standard position (S605: YES). The determination of S409 of FIG. 12(*b*) is therefore YES.

On the other hand, when the methanol is not replenished in the first methanol chamber 111 until the liquid surface reaches the standard position (S605: NO), the controller 201 alerts the user to replace the bottle 101 by a methanol replenishment error (S606). This alert is accomplished, for example, by displaying an alert screen on the operation display unit 2*a* (refer to FIG. 1). When a replenishment error is detected, transporting of the cassette 20 and dispensing of methanol to the cassette 20 are suspended.

Thereafter, the controller 201 awaits the replacement of the bottle 101 (S607). When the error alert is received the user replaces the bottle 101 with a fresh bottle 101 and thereafter, when, for example, replacement completed input is entered from the screen of the operation display 2*a* (S607: YES), the controller 201 replenishes the first methanol chamber 111 with fresh methanol from the new bottle 101 (S608). Methanol replenishment is thus started.

When the methanol is not replenished in the first methanol chamber 111 until the liquid surface reaches the standard position (S609: NO), the controller 201 alerts the user of a bottle replacement error (S611), and the controller 201 awaits proper installation of the new bottle 101 (S607). On the other hand, when the methanol is replenished in the first methanol chamber 111 until the liquid surface reaches the standard position (S609: YES), the controller 201 cancels the replenishment error (S610), and the replacement process ends. When a replenishment error is canceled, transporting of the cassette 20 and dispensing of methanol to the cassette 20 are restarted.

Note that in the replacement process of FIG. 14, the methanol is discharged from the first methanol chamber 111 after the recovery counter Ck has attained the threshold frequency C0 in S601 without immediately discharging the methanol from the first methanol chamber 111 even when the methanol replacement process has started in S405 of FIG. 12(*b*). This is done to prevent recovery of repeatedly used methanol in the first methanol chamber 111 after the replacement with fresh methanol. That is, a plurality of cassettes 20 are usually present from the position Mp to the position D1*p* with the timing of starting the methanol replacement process in S405 of FIG. 12(*b*). The methanol degraded through repeated use is dispensed from the first methanol chamber 111 to these cassettes 20. Therefore, it is not desirable to recover methanol to the first methanol chamber 111 after replacing the methanol from the cassettes 20.

In the present embodiment, discharge and replenishment of the methanol is not performed for the first methanol chamber 111 immediately until the recovery counter Ck has attained the threshold frequency C0 even though the methanol replacement process starts. The threshold frequency C0 is set so that the cassette 20 that has been dispensed unused methanol from the second methanol chamber 112 in S408 of FIG.

12(b) reaches the position D1p with the timing of the completion of the methanol replacement.

Note that the threshold frequency C0 is preset based on the time (immersion time) from the dispensing of the methanol to the cassette 20 at position Mp to the recovery of the methanol from the cassette 20 at position D1p. Therefore, recovery of pre-replacement degraded methanol in the first methanol chamber 111 immediately after methanol replacement is prevented by providing a time lag based on the threshold frequency C0 until the methanol replacement process is performed for the first methanol chamber 111.

Figure 15:
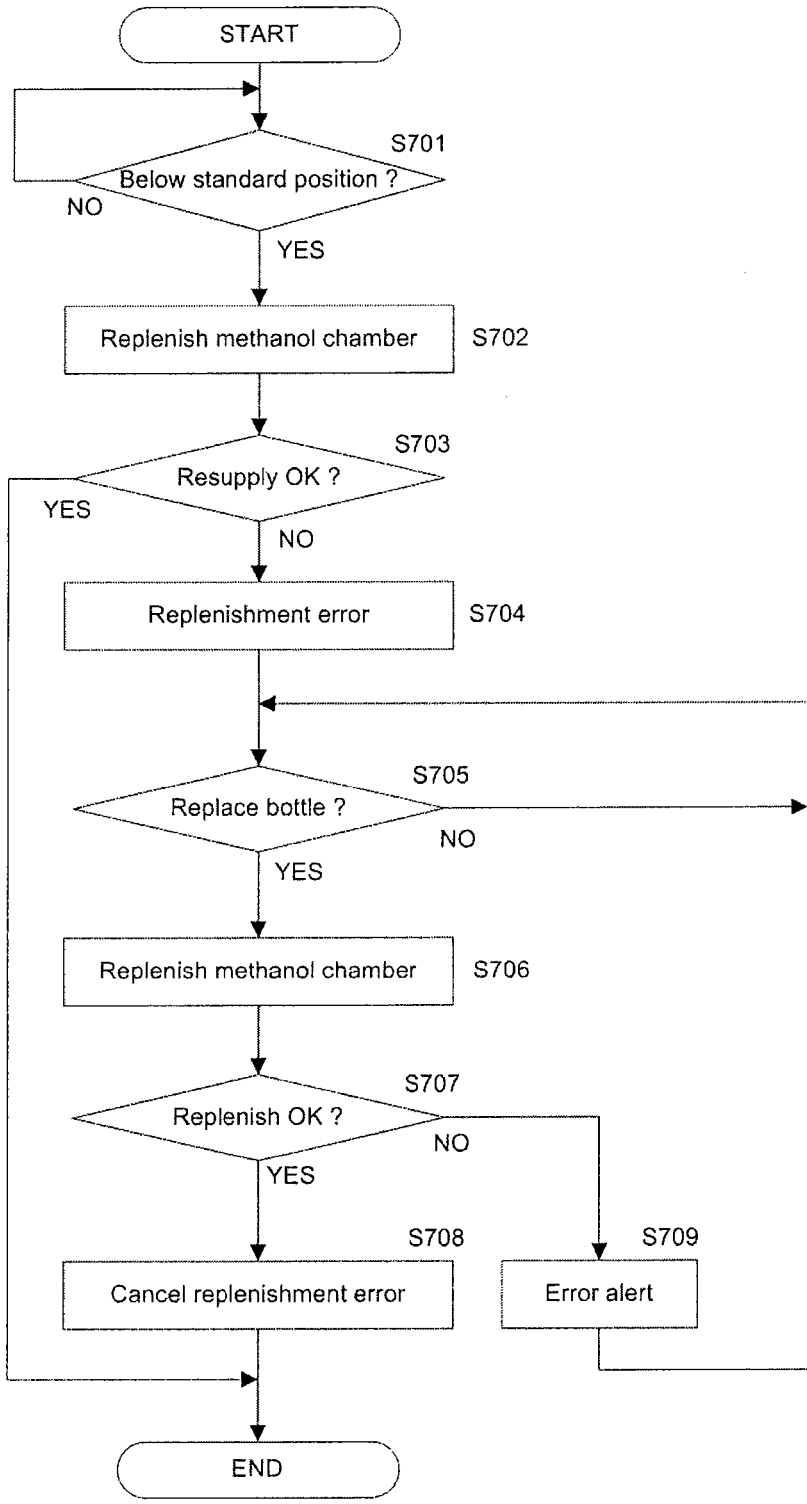
FIG. 15 is a flow chart of the methanol supplying process of the first methanol chamber and the second methanol chamber of the embodiment.

FIG. 15 is a flow chart showing the methanol replenishment process of the first methanol chamber 111 and second methanol chamber 112. The replenishment process is performed every time methanol is dispensed from the first methanol chamber 111 or second methanol chamber 112 to the cassette 20. Note that the description of the methanol replenishment process for the first methanol chamber 111 is identical to the methanol replenishment process for the second methanol chamber 112.

When the liquid surface in the first methanol chamber 111 falls below the standard position (S701: YES), the controller 201 supplies fresh methanol to the first methanol chamber 111 from the bottle 101 (S702). Methanol replenishment is thus started.

When the methanol is replenished in the first methanol chamber 111 until the liquid surface attains the standard position (S703: YES), the replenishment process ends. On the other hand, when the methanol is not replenished in the first methanol chamber 111 until the liquid surface reaches the standard position (S703: NO), the controller 201 alerts the user to replace the bottle 101 by a methanol replenishment error (S704). When a replenishment error is detected while washing a cassette, transporting of the cassette 20 and dispensing of methanol to the cassette 20 are suspended.

Thereafter, the controller 201 awaits the replacement of the bottle 101 (S705). When the error alert is received the user replaces the bottle 101 with a fresh bottle 101 and thereafter, when, for example, replacement completed input is entered from the screen of the operation display 2a (S705: YES), the controller 201 replenishes the first methanol chamber 111 with fresh methanol from the new bottle 101 (S706). When the methanol is not replenished in the first methanol chamber 111 until the liquid surface reaches the standard position (S707: NO), the controller 201 alerts the user of a bottle replacement error (S709), and the controller 201 awaits proper installation of the new bottle 101 (S705). On the other hand, when the methanol is replenished in the first methanol chamber 111 until the liquid surface reaches the standard position (S707: YES), the controller 201 cancels the replenishment error (S708), the process returns to S701 and the next replenishment timing is awaited. When a replenishment error is canceled, transporting of the cassette 20 and dispensing of methanol to the cassette 20 are restarted.

Figure 16:
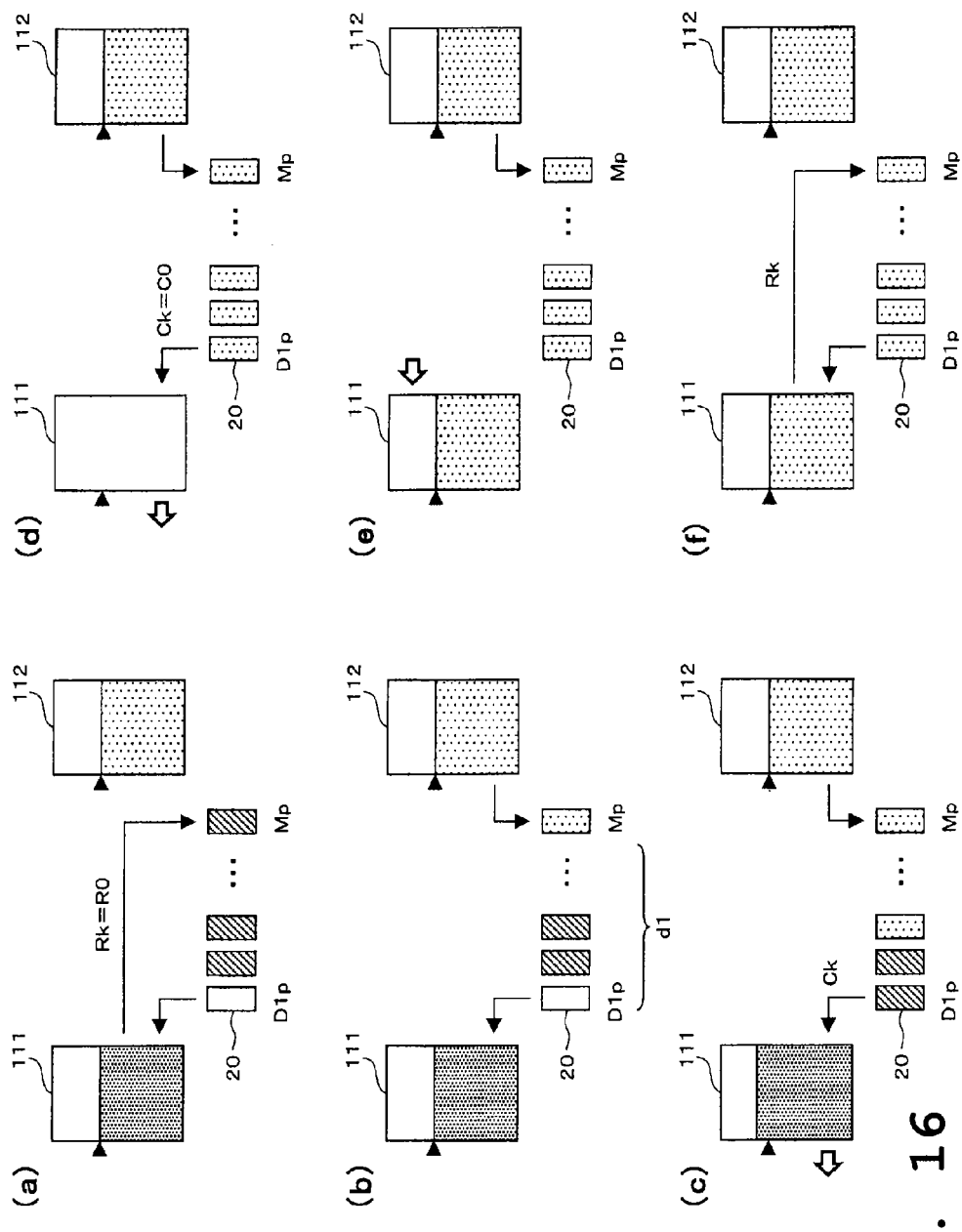
FIGS. 16(a)-16(f) show specific examples of the washing process of the embodiment.

FIG. 16 shows an example of the washing process.

As shown in FIG. 16(a), while the methanol is being reused, the methanol is dispensed from the first methanol chamber 111 to the cassette 20 at position Mp, and methanol is recovered from the cassette 20 to the first methanol chamber 111 at position D1p. When the reuse counter Rk attains the threshold frequency R0, processes are started during replacement and methanol is dispensed from the second methanol chamber 112 to the cassette 20 at position Mp, and methanol is recovered from the cassette 20 to the first methanol chamber 111 at position D1p, as shown in FIG. 16(b). At this time the is at most dl individual cassettes 20 present between the position Mp and the position D1p. This process is repeated until the recovery counter Ck attains the threshold frequency C0. During this time, when the methanol retained in the first methanol chamber 111 exceeds the standard position, the methanol is discharged from the first methanol chamber 111 as shown in FIG. 16(c).

Thereafter, when the recovery counter Ck attains the threshold frequency C0, the methanol is discharged from the first methanol chamber 111 as shown in FIG. 16(d). At this time methanol from the second methanol chamber 112 is dispensed to the cassette 20 at position Mp. Thereafter, when methanol is replenished to the first methanol chamber 111 to the standard position as shown in FIG. 16(e), the process is switched during reuse and the process using the first methanol chamber is restarted as shown in FIG. 16(f).

According to the present embodiment described above, washing of all cassettes 20 placed in the cassette receiver 47 is performed automatically by pressing the cassette wash start button 402 when the empty cassette 20 has been placed in the cassette receiver 47. Therefore, the labor required to wash the cassette 20 is greatly reduced.

According to the present embodiment, the cassette 20 washing process is skipped when a slide glass 10 is detected in the cassette 20 via the sensor 48s during the cassette washing process. Therefore, washing a cassette 20 without removing the slide glass after preparing the smear sample can be avoided even when the cassette 20 is placed in error in the cassette receiver 47.

According to the present embodiment, during the washing process the methanol dispensed to the cassette 20 is recovered through the recovery pipette D1b and the methanol of the first methanol chamber 111 is reused. Thus, the consumption of methanol is reduce compared to when methanol is discarded with each washing. This also reduces the environmental burden.

Although described in terms of the present embodiments, the present invention is not limited to these embodiments.

For example, although a single slide glass 10 (smear sample) is accommodated in a single cassette 20 in the above embodiment, the present invention is not limited to this arrangement inasmuch as a plurality of slide glasses 10 (smear samples) also may be accommodated.

Although another process cannot be performed while one of the smear sample preparation process (S12) and cassette washing process (S14) is being performed in the present embodiments, the present invention is not limited to this configuration inasmuch as another process may be performed through an interrupt while performing one process. For example, the smear sample preparation process may be performed through an interrupt even during an ongoing cassette washing process. In this case, a sample can be rapidly prepared when an urgent sample preparation is required during an ongoing cassette washing process.

In the above embodiments, the process of replacing the first methanol chamber 111 is started when the methanol reuse frequency (reuse counter Rk) attains a preset frequency (threshold frequency R0) while methanol is reused (S107 of FIG. 8). When the liquid surface of the first methanol chamber 111 is below a standard position while methanol is being reused, methanol is resupplied to the first methanol chamber 111 until the liquid surface attains the standard level (S402 of FIG. 12). However, the present invention is not limited to this configuration inasmuch as methanol replenishment need not be performed when the liquid surface of the first methanol chamber 111 is below the standard position while methanol is being reused. In this case, the process for replacing the first methanol chamber 111 may be performed based on the amount of remaining methanol in the first methanol chamber 111 and need not be performed in accordance with the methanol reuse frequency (reuse counter Rk).

Although the connection of the flow passes shown in FIG. 5 are switched by valves in the above embodiments, the present invention is not limited to this configuration inasmuch as syringe pumps may be respectively provided to the flow passes to switch the connections of the flow passes by switching the actuation of the syringe pumps.

Although the methanol recovered from the cassette 20 through the recovery pipette D1b is moved to the first methanol chamber 111 in the above embodiments, the present invention is not limited to this configuration inasmuch as the recovered methanol also may be moved to a chamber other than the first methanol chamber 111. In this case, the methanol moved to another chamber also may be reused. The recovered methanol also may be recovered in the discard chamber 165 so as to be discharged from the smear sample preparation device 2.

Although dispensing and recovery of the methanol to/from the cassette 20 is performed once each in the cassette washing process of the above embodiments, the present invention is not limited to this configuration inasmuch as dispensing and recovery may be performed a plurality of times. The cassette 20 containing the methanol also may be shaken in the cassette washing process. Shaking the cassette 20 may be performed by, for example, moving the belt 50b forward and back, or changing the lateral height of the belt 50b via another mechanism. Methanol in the cassette 20 also may be caused to flow in the cassette washing process. The flow of the methanol may be induced by, for example, repeatedly dispensing and discharging the methanol in the cassette 20 via the recovery pipette D1b at position D1p. This operation reliably washes the cassette 20.

Although methanol is used to fix the sample when washing the cassette 20 in the above embodiments, the present invention is not limited to this configuration inasmuch as a washing liquid other than methanol (for example, water) also may be used. Note that when was is used as the washing liquid, it is preferable to perform a process to dry the interior of the cassette 20 after the water is recovered from the cassette 20.

Although the cassette 20 is moved to the positions Mp and D1p by the belt 50b in the above embodiments, the present invention is not limited to this configuration inasmuch as the dispensing and recovery of methanol also may be performed while the cassette 20 is positioned at a predetermined position. In this case, for example, a pipette for dispensing methanol and a pipette for recovering methanol may be moved to the position of the cassette 20 and dispensing and discharge of the methanol may be performed at that position.

Although the same threshold frequency R0 is used in the staining process and the washing process in the above embodiments, the present invention is not limited to this configuration inasmuch as different threshold frequencies also may be used. In this case, tolerance ranges can be set relative to the degrading of the reused methanol for both the staining process and the washing process, respectively. For example, a lower threshold frequency may be set for the washing process than for the staining process. In this case, the washing process is performed with less degraded methanol.

Note that, in the above embodiments, when the washing operation is started after the staining operation, the incrementation by S403 was made on the reuse counter Rk incremented in S403 of FIG. 10b). However, the present invention is not limited to this configuration inasmuch as the washing operation may be started after the methanol in the first methanol chamber 11 has been replaced with fresh methanol and the reuse counter Rk has been reset.

Although the smear sample preparation process is performed when a user presses the sample preparation start button 401 (FIG. 9(a)) in the above embodiments, the present invention is not limited to this configuration inasmuch as the process also may be performed when the smear sample preparation device 2 receives a smear sample preparation instruction. For example, the clinical sample processing apparatus 1 of the above embodiment may be used as part of a sample processing system that includes a plurality of analyzers and a transport controller for controlling transport. In this case, the smear sample preparation process also may be performed when the controller 201 of the smear sample preparation device 2 receives a smear sample preparation instruction from the transport controller, or when the controller 201 receives a smear preparation instruction sent from the transport controller via the transport device 3.

Although the above embodiments are configured to display a sample preparation start button and a cassette wash start button as software keys on the display unit, these buttons also may be implemented as hardware keys on the device.

The embodiments of the present invention may be variously and appropriately modified insofar as such modification is within the scope of the meaning expressed in the claims.

What is claimed is:
1. A slide processing apparatus comprising:
a stocker capable of stocking one or more housing elements;
a slide supplier configured to supply a slide in the housing element;
a liquid transporter configured to transport a staining liquid reserved in a first liquid container and/or a washing liquid reserved in a second liquid container to the housing element;
a first instruction receiver for receiving a first instruction that instructs to initiate staining of a slide accommodated in a housing element with the staining liquid;
a second instruction receiver for receiving a second instruction that instructs to initiate washing of the housing element;
a slide detector for detecting a slide accommodated in the housing element received from the stocker; and
a controller,
wherein the controller is programmed to perform supplying of a slide to the housing element by actuating the slide supplier and to perform staining of the slide by causing the liquid transporter to transport the staining liquid into the housing element, upon receiving the first instruction;
the controller is programmed to perform washing of the housing element by causing the liquid transporter to transport the washing liquid into the housing element, upon receiving the second instruction; and
the controller is programmed to control the liquid transporter so that the washing liquid is not supplied to the housing element when a slide is detected in a housing element upon receiving the second instruction.
2. The slide processing apparatus of claim 1, wherein the housing element accommodates only a single slide.
3. The slide processing apparatus of claim 1, wherein the housing element is provided with a slit on an upper side of the housing element for receiving therethrough a slide in a manner where a surface of the slide on which a sample is smeared directs horizontally.

4. The slide processing apparatus of claim 1, further comprising a display unit;
wherein the controller is programmed to cause the display unit to display the first instruction receiver and the second instruction receiver on the display unit.

5. The slide processing apparatus of claim 4, wherein
the controller is programmed to cause the display unit to display an indication that the apparatus is currently performing washing when receiving the second instruction.

6. The slide processing apparatus of claim 1, further comprising:
a housing element transporter configured to transport the housing element to a first supply position where the housing element is supplied with a staining liquid by the liquid transporter and a second supply position where the housing element is supplied with a washing liquid by the liquid transporter, and
the controller is programmed to cause the housing element transporter to transport the housing element to the second position and causes the liquid transporter to transport the washing liquid to the housing element at the second position when receiving the second instruction.

7. The slide processing apparatus of claim 6, wherein
the stocker is capable of providing the stocked housing element to the housing element transporter,
when receiving the first instruction, the controller is programmed to cause the housing element transporter to transport the housing elements in the stocker to the first position when receiving the first instruction, and
the controller is programmed to cause the housing element transporter to transport the housing elements in the stocker to the second position when receiving the second instruction.

8. The slide processing apparatus of claim 7, wherein
the controller is programmed to cause the housing element transporter to sequentially transport all housing elements in the stocker to the second position when receiving the second instruction.

9. The slide processing apparatus of claim 1, wherein
the slide detector comprises a light emitter and a light receiver arranged along a transport path of the housing element, the light emitter and the light receiver being arranged both sides of the transport path,
the slide detector detects a slide when a beam of light which is emitted from the light emitter toward the light receiver is blocked by the slide accommodated in the housing element.

10. The slide processing apparatus of claim 1, wherein
the washing liquid is usable for washing a housing element and for fixing a sample smeared on a slide,
the controller is programmed to cause the liquid transporter to supply the washing liquid to the housing element to fix the slide, and thereafter causes the liquid transporter to supply the staining liquid to the housing element to stain the fixed sample when receiving the first instruction.

11. The slide processing apparatus of claim 10, wherein
the controller is programmed to cause the liquid transporter to supply a first amount of the washing liquid to the housing element for fixing a sample
and to cause the liquid transporter to supply a second amount of washing liquid to the housing element for washing the housing element, and
the second amount is greater than the first amount.

12. The slide processing apparatus of claim 1, wherein
the liquid transporter further comprises a force generator for generating a transport force to transport a staining liquid and a washing liquid, a flow path through which to transport the staining liquid and the washing liquid, and a switching part for switching the flow path in which the staining liquid and the washing liquid flows.

13. The slide processing apparatus of claim 1, further comprising a smear unit for smearing a sample on a slide.

14. A slide processing apparatus comprising:
a stocker capable of stocking one or more housing elements;
a slide supplier configured to supply a slide in the housing element;
a liquid transporter configured to transport a staining liquid reserved in a first liquid container and/or a washing liquid reserved in a second liquid container to the housing element;
a first instruction receiver for receiving a first instruction that instructs to initiate staining of a slide accommodated in a housing element with the staining liquid;
a second instruction receiver for receiving a second instruction that instructs to initiate washing of the housing element; and
a controller;
wherein the controller is programmed to perform supplying of a slide to the housing element by actuating the slide supplier and to perform staining of the slide by causing the liquid transporter to transport the staining liquid into the housing element, upon receiving the first instruction;
the controller is programmed to perform washing of the housing element by causing the liquid transporter to transport the washing liquid into the housing element, upon receiving the second instruction;
the controller is programmed to cause the housing element transporter to transport the housing elements in the stocker to the second position when receiving the second instruction;
the controller is programmed to cause the liquid transporter to supply the washing liquid to the housing element, and thereafter to recover the washing liquid in the housing element when receiving the second instruction; and
the controller is programmed to cause the liquid transporter to supply the washing liquid which has been used and recovered from the one housing element to another housing element for executing sequential washing of two or more housing elements.

15. The slide processing apparatus of claim 14, wherein
the first liquid container contains unused washing liquid,
the controller is programmed to cause the liquid transporter to transport the washing liquid recovered from the one housing element to a third liquid container, and
for executing washing of the another housing element, the controller is programmed to cause the liquid transporter to transport the washing liquid retained in the third liquid container to the other housing element.

16. The slide processing apparatus of claim 15, wherein
the controller is programmed to cause the liquid transporter to discards the washing liquid in the third liquid container when the number of times of reuse of the washing liquid in the third liquid container reaches a predetermined number.

17. The slide processing apparatus of claim 15, wherein
the controller is programmed to cause the liquid transporter to supply the washing liquid from the first liquid container to the housing element to be washed when the number of times of reuse of the washing liquid in the third liquid container reaches a predetermined number.

18. A slide processing apparatus comprising:
- a liquid transporter configured to transport a staining liquid reserved in a first liquid container and/or a washing liquid reserved in a second liquid container to a housing element capable of housing therein a slide to be stained with the staining liquid;
- a slide detector for detecting a slide accommodated in the housing element; and
- a controller programmed to control the liquid transporter under a plurality of operating modes including at least a staining mode and a washing mode,
- wherein the controller is programmed to cause the liquid transporter to transport the staining liquid to the housing element under the staining mode and to cause the liquid transporter to transport the washing liquid to the housing element under the washing mode, and wherein the controller is programmed to control the liquid transporter so that the washing liquid is not supplied to the housing element when a slide is detected in a housing element under the washing mode.

19. The slide processing apparatus of claim 18 wherein the washing liquid is methanol.

* * * * *